(12) United States Patent
Battlogg

(10) Patent No.: US 10,975,926 B2
(45) Date of Patent: *Apr. 13, 2021

(54) HAPTIC OPERATING DEVICE WITH A ROTATING ELEMENT AND METHOD FOR OPERATING ELECTRONIC EQUIPMENT WITH THE HAPTIC OPERATING DEVICE

(71) Applicant: INVENTUS ENGINEERING GMBH, St. Anton I.M. (AT)

(72) Inventor: Stefan Battlogg, St. Anton I.M. (AT)

(73) Assignee: INVENTUS Engineering GmbH, St. Anton i.M. (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/691,711

(22) Filed: Nov. 22, 2019

(65) Prior Publication Data
US 2020/0088251 A1   Mar. 19, 2020

Related U.S. Application Data

(60) Division of application No. 16/014,223, filed on Jun. 21, 2018, now Pat. No. 10,502,271, which is a
(Continued)

(30) Foreign Application Priority Data

Sep. 15, 2010 (DE) .............................. 102010045436
Dec. 23, 2010 (DE) .............................. 102010055833
Jul. 1, 2015 (DE) .......................... 102015110633.7

(51) Int. Cl.
*F16D 37/02* (2006.01)
*F16C 33/66* (2006.01)
(Continued)

(52) U.S. Cl.
CPC ................ *F16D 37/02* (2013.01); *A61F 2/68* (2013.01); *F16C 33/6688* (2013.01);
(Continued)

(58) Field of Classification Search
None
See application file for complete search history.

(56) References Cited

U.S. PATENT DOCUMENTS 5,191,811 A   3/1993 Kogure
5,816,372 A   10/1998 Carlson et al.
(Continued)

FOREIGN PATENT DOCUMENTS

DE   19528457 A1   2/1997
DE   10245354 A1   4/2004
(Continued)

*Primary Examiner* — Matthew Yeung
(74) *Attorney, Agent, or Firm* — Laurence A. Greenberg; Werner H. Sterner; Ralph E. Locher

(57) ABSTRACT

Electronic devices, such as consumer electronics devices and constrol systems in vehicles are controlled by way of a haptic operating device with a rotating unit. Selectable menu items are displayed on a display unit, and a menu item is selected by rotating the rotating unit. The rotating unit latches at a number of haptically perceptible latching points during rotation. The number and rotational position of the haptically perceptible latching points is dynamically changed in accordance with a specific menu item selected by the user.

8 Claims, 5 Drawing Sheets

Related U.S. Application Data continuation-in-part of application No. 15/200,918, filed on Jul. 1, 2016, now Pat. No. 10,007,290, which is a continuation-in-part of application No. 14/747,025, filed on Jun. 23, 2015, now Pat. No. 10,318,002, which is a continuation-in-part of application No. 13/823,781, filed as application No. PCT/EP2011/004623 on Sep. 15, 2011, now Pat. No. 9,091,309.

(51) Int. Cl.
| | | |
|---|---|---|
| *F16D 57/00* | (2006.01) | |
| *A61F 2/68* | (2006.01) | |
| *G06F 3/01* | (2006.01) | |
| *G06F 3/0362* | (2013.01) | |
| *F16C 41/00* | (2006.01) | |
| *F16D 37/00* | (2006.01) | |
| *A61F 2/50* | (2006.01) | |
| *F16C 19/06* | (2006.01) | |
| *A61F 2/70* | (2006.01) | |

(52) U.S. Cl.
CPC .......... *F16C 41/001* (2013.01); *F16D 57/002* (2013.01); *G06F 3/016* (2013.01); *G06F 3/0362* (2013.01); *A61F 2/70* (2013.01); *A61F 2002/5004* (2013.01); *F16C 19/06* (2013.01); *F16C 2210/06* (2013.01); *F16D 2037/002* (2013.01); *F16D 2037/005* (2013.01)

(56) References Cited

U.S. PATENT DOCUMENTS

| | | | | |
|---|---|---|---|---|
| 5,936,613 | A * | 8/1999 | Jaeger | G06F 3/0238 345/172 |
| 5,944,151 | A | 8/1999 | Jakobs et al. | |
| 6,119,553 | A | 9/2000 | Yamagishi et al. | |
| 6,636,197 | B1 | 10/2003 | Goldenberg | G05G 1/02 345/156 |
| 6,682,217 | B1 | 1/2004 | Joffe | |
| 7,579,559 | B2 | 8/2009 | Schelbert et al. | |
| 9,091,309 | B2 | 7/2015 | Battlogg | |
| 2002/0057152 | A1 * | 5/2002 | Elferich | G05G 1/08 335/220 |
| 2003/0048254 | A1 * | 3/2003 | Huang | G06F 3/03543 345/163 |
| 2004/0061463 | A1 | 4/2004 | Hayasaka | G06F 3/016 318/280 |
| 2005/0156892 | A1 | 7/2005 | Grant | G06F 3/016 345/167 |
| 2006/0055582 | A1 | 3/2006 | Wendt | |
| 2006/0071917 | A1 | 4/2006 | Gomez | G06F 3/016 345/184 |
| 2006/0132469 | A1 * | 6/2006 | Lai | B60K 35/00 345/184 |
| 2007/0236450 | A1 | 10/2007 | Colgate | G06F 3/016 345/156 |
| 2008/0202906 | A1 | 8/2008 | Schelbert | B60K 37/06 200/308 |
| 2009/0167508 | A1 | 7/2009 | Fadell | G06F 3/016 340/407.2 |
| 2009/0184925 | A1 * | 7/2009 | Chien | G06F 3/03543 345/163 |
| 2010/0288072 | A1 | 11/2010 | Springer | G06F 3/016 74/552 |
| 2012/0138407 | A1 | 6/2012 | Seipel et al. | |
| 2012/0242626 | A1 * | 9/2012 | Hu | G06F 1/163 345/184 |
| 2013/0175132 | A1 | 7/2013 | Battlogg | |
| 2016/0216763 | A1 | 7/2016 | Vanhelle et al. | |

FOREIGN PATENT DOCUMENTS

| | | |
|---|---|---|
| DE | 102006018518 A1 | 2/2007 |
| DE | 102010055833 A1 | 3/2012 |
| EP | 1168622 A2 | 1/2002 |
| WO | 2012034697 A1 | 3/2012 |
| WO | 2015033034 A1 | 3/2015 |

* cited by examiner

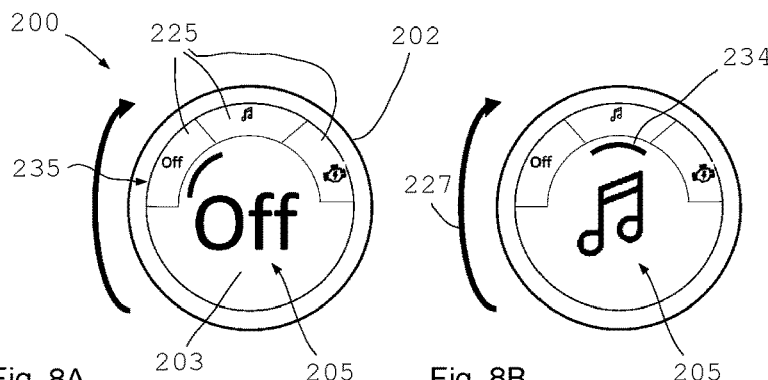
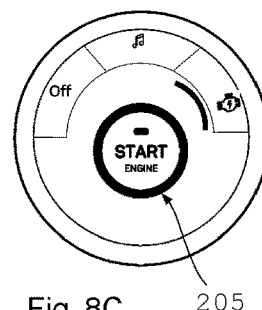
Fig. 8A  Fig. 8B  Fig. 8C
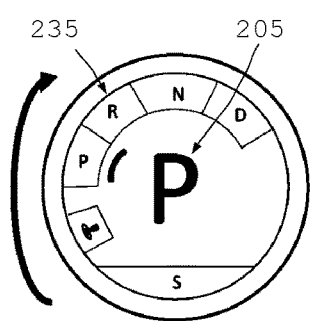
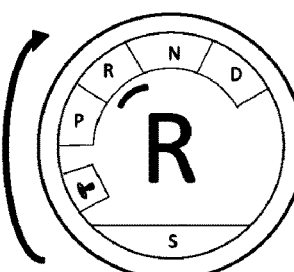
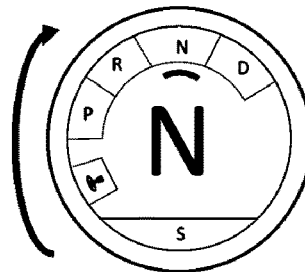
Fig. 8D  Fig. 8E  Fig. 8F
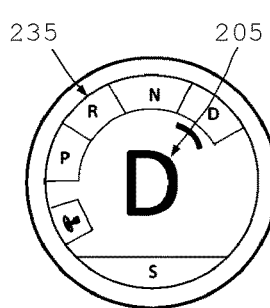
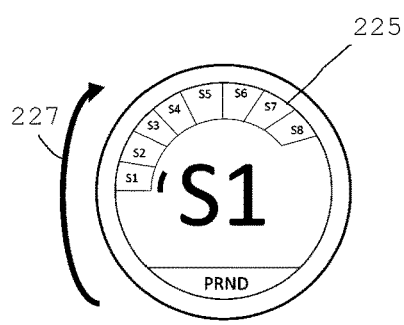
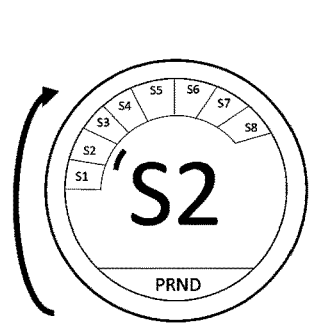
Fig. 8G  Fig. 8H  Fig. 8I
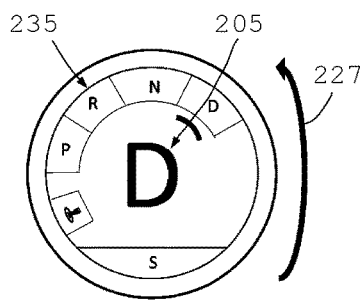
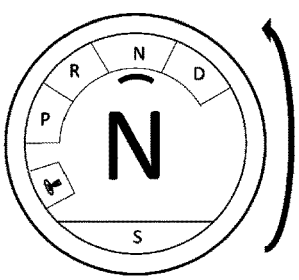
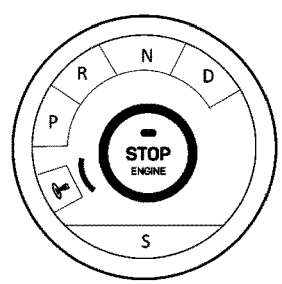
Fig. 8J  Fig. 8K  Fig. 8L

HAPTIC OPERATING DEVICE WITH A ROTATING ELEMENT AND METHOD FOR OPERATING ELECTRONIC EQUIPMENT WITH THE HAPTIC OPERATING DEVICE

CROSS-REFERENCE TO RELATED APPLICATIONS

This application is a divisional of copending patent application Ser. No. 16/014,223, filed Jun. 21, 2018, which was a continuation-in-part of patent application Ser. No. 15/200,918, filed Jul. 1, 2016, now U.S. Pat. No. 10,007,290 B2; which was a continuation-in-part of copending patent application Ser. No. 14/747,025, filed Jun. 23, 2015; which was a continuation-in-part of patent application Ser. No. 13/823,781, filed Mar. 15, 2013, now U.S. Pat. No. 9,091,309 B2, issued Jun. 28, 2015; which was a § 371 national stage of international patent application PCT/EP2011/004623, filed Sep. 15, 2011; this application further claims the priority of German patent applications DE 10 2010 045 436, filed Sep. 15, 2010, DE 10 2010 055 833, filed Dec. 23, 2010, and DE 10 2015 110 633.7, filed Jul. 1, 2015; the prior applications are herewith incorporated by reference in their entirety.

BACKGROUND OF THE INVENTION

Field of the Invention

The present invention relates to a haptic operating device having a transmission apparatus and, in particular, a force or torque transmission apparatus, wherein the transmission between a first component and at least one second component which is stationary or moves relative to the first component is able to be changed by influencing the transmission properties between the components. The haptic operating device according to the invention can be used in various technical fields, for example for operating technical equipment such as vehicles or industrial installations or for operating washing machines, kitchen appliances, radios, hi-fi systems or other devices.

In one embodiment of the force or torque transmission, there is provided a magnetorheological transmission in which the transmission property is affected by a magnetorheological fluid that is subjected to a magnetic field. Magnetorheological fluids have very fine ferromagnetic particles, for example carbonyl iron powder, distributed in an oil, for example. Spherical particles having a production-related diameter of 1 to 10 micrometers are used in magnetorheological fluids, in which case the particle size is not uniform. If a magnetic field is applied to such a magnetorheological fluid, the carbonyl iron particles of the magnetorheological fluid are concatenated along the magnetic field lines, with the result that the rheological properties of the magnetorheological fluid (MRF) are considerably influenced depending on the form and strength of the magnetic field.

With regard to the background relating to the embodiments of the invention with the magnetorheological transmission, reference is had to the above-noted prior applications and to information detailed therein.

It has been found during many tests that a haptic operating element can be used commercially as a standard product for infotainment in automobiles, for rotating actuators on smart devices or as an actuator on devices (for example: oscilloscope), for example, virtually only when the base torque (idling torque with the magnetic field switched off; off-state torque) is less than 0.1 Newton meters (Nm). This applies to typical rotary knob diameters of 30, 40 or 50 mm. If a particularly small rotary knob diameter (for example <5 or 10 mm) is used, a base torque considerably lower than 0.1 Nm is very advantageous and necessary.

Haptic operating elements, in particular rotating actuators in vehicles or on smart devices, require, for standard use which is accepted by the user, a base torque which is many times smaller than in the prior art (MRF brakes according to the shearing principle); these base torques are below 0.2 Nm and better less than 0.1 Nm and ideally below 0.05 Nm. Fingers are very sensitive in this regard. For comparison, the haptic operating range (a fine latching pattern) of a known and purely mechanical rotating actuator (benchmark in automobiles) having a knob diameter of approximately 50 mm is between approximately 0.01 Nm (base torque) and a maximum torque of 0.05 Nm (peak ripple). A conventional infotainment rotary knob in the center console (rotating actuator with a rotary knob diameter of 50 mm, for example) with a base torque of 0.06 Nm is not accepted by many automobile manufacturers (cannot be commercially implemented). The necessary blocking (at least 5 Nm, for example simulation of an end stop or the position "P" in the gear selector switch) must then be produced using an additional locking pin (electrically actuated lifting magnet), for example.

A preferred object is therefore to provide an adaptive operating element, the braking torque of which can preferably be set between 0.02 Nm (or less) and 5 Nm (=operating range) in the millisecond range. A factor in the region of 250 between the base torque and the maximum torque is therefore required, which is more than 12 times more than that in the prior art.

In the automotive industry in particular, the intention is to reduce the number of operating knobs in the vehicle since the number has greatly increased on account of the multiplicity of functions. The aim is to substantially display only the currently required information and switching options. On the other hand, the customer should not have to enter and browse the menus too much in order to be able to carry out necessary functions. Therefore, the user must often be able to operate a haptic operating element without the use of force.

BRIEF SUMMARY OF THE INVENTION

The object of the invention is therefore to improve the advantageous variability and flexibility of haptic operating devices in such a manner that they can be used for sophisticated haptic operating elements.

For good form, the term "haptic" relates to the sense of touch and it relates, in particular, to manipulating and perceiving objects using touch and proprioception.

With the above and other objects in view there is provided, in accordance with the invention, a haptic interface, comprising:

a rotary element to be manually activated;

an integrated rotary encoder associated with said rotary element and disposed to interpret a rotation of said rotary element upon manual activation thereof;

and a display for displaying a given selected menu;

wherein at least one property of the haptic interface changes depending on a currently selected menu, wherein the at least one property of the haptic interface is a resistance of said rotary element against rotation thereof, and the resistance is variably set to provide a haptic feedback to the manual activation of said rotary element and in accordance with the currently selected menu.

In a preferred embodiment, I provide a haptic operating device having a magnetorheological transmission apparatus, thus enabling even more flexible use. While the description below refers repeatedly to the implementation of the invention within the magnetorheological transmission domain, it is not limited to the same, as other transmission and conversion technologies may be adopted.

In the magnetic embodiment, there is provided a magnetic field concentrator that concentrates the magnetic field onto a smaller area. The transmission element may be in the form of a ball or roller, for example, without being restricted to these forms, and concentrates the magnetic field, that is to say the magnetic field is changed between the two components which are moved relative to one another and is concentrated from a large area onto a small area (a transition area). The ratio of these areas is considerably greater than 1 and, in particular, greater than 2, greater than 5 or, in particular, greater than 10. In principle, this is the ratio of the cylindrical area of the inner ring in relation to (the region of) the tangent edge of a roller or in relation to a ball point multiplied by a number of the transmission elements, in particular 15, for example.

The transmission element concentrates the magnetic field and forms a magnetic field or flux density concentrator.

The transmission element is connected neither to the first component nor to the second component in a rotationally fixed manner. The field concentrator can move "arbitrarily" between the two components.

Such a haptic operating device according to the invention has many advantages. The haptic operating device allows a very small base torque, thus making it possible to easily rotate the rotating unit or a rotary knob formed on the haptic operating device. An operator can conveniently rotate the rotating part using his little finger. A base torque which is less than 0.1 Nm and, in particular, less than 0.07 Nm and preferably less than 0.05 Nm is enabled, thus enabling convenient operation in daily use even if used frequently. It is not necessary to grip the rotating part using the entire hand or at least two fingers in order to rotate the rotating part (even repeatedly in succession). Simple touching and rotating using only one finger also generally suffice.

At the same time, a simple structure is enabled and only few parts are used. As a result of the simple structure, in which torque is transmitted through the magnetorheological medium or magnetorheological fluid (MRF) only inside the channel at least to the greatest extent, a particularly low base torque (base torque=torque needed for rotation when the electrical coil is switched off) can be achieved.

In contrast, a haptic operating element according to EP 1 168 622 A2 has the disadvantage that the base torque is very high because a very large amount of shearing area is used. The ratio of active area to useful area (shearing area) is very unfavorable. The shearing gap must be small for technological reasons, which in turn greatly increases the friction (fluid friction). The active shearing gap filled with MRF is very large.

In the present invention, the channel has a large radial extent (channel height), with the result that the base friction caused by the MRF per se, when the magnetic field is switched off or is low, is very low on account of the large radial extent. The large radial extent results in a large channel area. In contrast to this, however, the transmission/contact areas are very small. Only transmission elements (for example rollers) affect the moving and stationary parts. The channel is very large and has low fluid friction.

In the structure according to EP 1 168 622 A2, the very thin gap contains MRF, which has substantially worse coefficients of friction on account of the iron particles and high viscosity (similar to chocolate sauce). The structure according to EP 1 168 622 A2 resembles a sliding bearing and the structure resembles a rolling bearing here. A base torque of <0.1 Nm is not possible in the case of an MRF structure according to the shearing principle, which is intended to be able to be commercially used as a standard product.

In particular, the basic body comprises a base plate and an annular holding housing with a holding space arranged in the latter, the holding space being radially delimited to the outside by an outer limb of the holding housing extending substantially in the axial direction. The shaft is preferably rotatably held centrally on the holding housing. In particular, the electrical coil is held in the holding space. In particular, a circumferential ring which is connected to the shaft in a rotationally fixed manner adjoins the holding housing in a radially inner region and in a manner separated by a thin axial gap. The channel is preferably arranged in the holding space and is radially delimited to the outside at least substantially or completely by the outer limb and is radially delimited to the inside at least substantially or completely by the circumferential ring, with the result that a substantial part of the magnetic field from the magnetic field generation device runs through the holding housing, the channel and the circumferential ring.

At least one display unit is preferably assigned. The rotating unit preferably surrounds a display unit at least in sections.

At least one actuation sensor for sensing an axial actuation force and/or an axial actuation travel is preferably arranged on the basic body and/or the rotating unit.

The cited haptic operating devices have many advantages. A haptic operating device in which the rotating unit surrounds a display unit at least in sections or else completely is very advantageous since the user has a view of the display unit, in particular directly in the center of the rotating unit. As a result, the user can observe the changing display of the display unit during rotation of the rotating unit and need not allow his gaze to stray in order to track what effects the rotation of the rotating unit has on the technical equipment such as, in particular, a vehicle and particularly preferably a motor vehicle. The user can also rotate the rotating unit without looking at the operating device and can possibly operate and actuate the rotating unit without visual contact. However, the user always has the possibility of ascertaining, by means of a brief glance, the position in which the rotating unit is currently situated and what is currently displayed on the display unit of the haptic operating device. A considerable further advantage is that the user can use his operating hand to partially cover a display field behind it, whereas that display area of the display unit which is enclosed by the rotating unit is usually nevertheless freely accessible to the user's gaze.

When used in a motor vehicle, for example, the haptic operating device according to the invention makes it possible for the start menu (OFF-infotainment-ignition-start) to be hidden after the starting process since it is no longer required as long as the automobile is moving. It is not even permissible to switch off or start the vehicle when the gear is engaged.

In the case of self-driving vehicles for example, there is a desire for the gear shifter to disappear or for the gear shift etc. to be hidden during "self-driving". In this case too, operation using the haptic operating device can now be dynamically (adaptively) adapted to the situation. Instead of the gear shift, it is possible to display the entertainment or, for example, parameters relevant to self-driving, for example distance, response behavior of the sensors etc.

In the case of self-driving vehicles or during autonomous driving, it may be problematic or dangerous if, for example, the vehicle containing the driver as the passenger automatically parks and the transmission selection lever for the gear shift remains here in the position selected last (for example "D") for mechanical reasons even though the vehicle is in the reverse gear. It is no longer possible for the driver to intervene here since the displayed function does not match the executed function, which can confuse the driver. This also applies to the process of switching on the light (rotary switch) which is autonomous or is required during or for self-driving, the windshield wipers, the gas pedal, the brake pedal or other systems. Therefore, the practice of making all switching elements active using servo motors is much too expensive. The invention provides a remedy since the gear shift can be automatically changed to the parked position "P" when a vehicle is switched off. In contrast, the rotating unit can remain in the position in which it is situated when the vehicle is switched off. The next time the vehicle is started, the current position is interpreted as "P".

In the case of automobiles, owing to the concentration on the road, it is also necessary for particular operating elements to be able to be actuated virtually "without looking" (that is to say "blind"). Haptic feedback additionally helps in this case.

The display unit is particularly preferably designed to display a symbol which is characteristic of a position of the rotating unit and is, in particular, a graphical symbol. It is possible for the display unit to display an operating state of the rotating unit and/or of the apparatus to be operated, such as a vehicle or a motor vehicle. It is possible and preferred for the operating state to be represented using a graphical symbol.

In all cases and configurations, the rotating unit can also be referred to as an operating unit.

A considerable advantage of a haptic operating device in which an actuation sensor for sensing an axial actuation is arranged is the fact that the haptic operating device cannot only be actuated by rotating the rotating unit but can also react to axial actuation forces. In such configurations having an actuation sensor, the actuation sensor is provided on and is particularly preferably fastened to the basic body and/or the rotating unit, in particular. The actuation sensor may sense an axial movement of the rotating unit relative to the basic body.

In particularly preferred configurations, a haptic operating device has a display unit on the rotating unit and at least one actuation sensor for sensing an axial actuation force.

The display unit is preferably connected to the basic body in a rotationally fixed manner, and the rotating unit is rotatable relative to the display unit. Such a configuration has the advantage that a display on the display unit does not change its angle during rotation of the rotating unit. As a result, the display on the display unit remains readable for the user in unchanged form. However, it is likewise possible for the display unit to be connected to the rotating unit in a rotationally fixed manner and to be rotatable, together with the rotating unit, with respect to the basic body. In the case of such a configuration, the viewing angle for the user does not change or changes only slightly if it at least partially rotates together with the rotating unit.

In preferred developments, at least one sensor which is used as an angle sensor is provided, which sensor can be used to sense an angle change between the rotating unit and the basic body. In this case, the sensor or angle sensor can detect relative angle changes. However, it is also possible for the sensor or angle sensor to sense an absolute angle between the rotating unit and the basic body. It is also possible for the sensor or angle sensor to sense an angle of between 0 and 360° in absolute terms, for example, but to be reset again after one complete revolution, with the result that angles of between 0 and 360° are always sensed during continuous rotation.

The sensor or the sensor used as an angle sensor preferably comprises at least two sensor parts, one sensor part being connected to the rotating unit and the other sensor part being connected to the basic body, in particular. For example, one sensor part may be in the form of a pulse generator, a measuring tape, a scale or the like and the other sensor part or the second sensor part may be used as a sensor or detector and may sense a relative movement of the first sensor part.

In preferred developments, the sensor or angle sensor is designed to sense an absolute angle position between the rotating unit and the basic body.

It is preferably possible to detect the direction of rotation. A high angular resolution is preferably possible. The finer the angular resolution, the earlier it is possible to recognize (or speculate) the wishes of the operator (reversal of the direction of rotation, finer adjustment). The control device (electronics/software) can react accordingly. A Hall sensor (EP 1 168 622 A2) is generally much too inaccurate for this purpose since only a few hundred "counts/revolution" are possible. The sensor or angle sensor is preferably designed to enable an angular resolution of 0.2° and, in particular, at least 0.1° or 0.05° or better. Angular resolutions of more than 100,000 "counts/revolution" (better than approximately $\frac{1}{300}$ degree) are desirable. With an angular resolution of better than 0.2° or 0.1°, a movement pattern can be derived from extremely small movements.

In the case of low sensor resolutions, the "operating element" or the rotating unit or the rotary knob can remain with a "sticking" feeling (a high torque is needed for actuation), which haptically feels very unpleasant and is therefore very disadvantageous. In the case of a reversal of the direction of rotation at an end stop, for example, a high torque must then be initially applied even though the user wishes to carry out rotation in the opposite direction and a release can therefore be effected. Only the control device must initially "notice" that rotation is being carried out in the opposite direction. In this case, a high angular resolution helps considerably.

The (visible) part of the rotary knob (visible part of the rotating unit) particularly preferably does not form part of the magnetic circuit. The visible part of the rotary knob can particularly preferably have any desired design; the rotary knob can be chromium-plated or can be made of plastic or glass or can be covered with leather etc. since the rotary knob is a "design element". This also relates to the assembly suitability (no screws visible; covering of the assembly hole etc.).

The transmission elements or rotating bodies (running rollers) are preferably rounded or cambered on the end face so that they axially have only point contact with the base plate or the cover. This considerably reduces the base friction and therefore the base torque.

It is possible to dispense with a contact ring.

The shaft is preferably magnetically conductive, thus reducing the size, weight and costs. The shaft preferably consists of a low-alloy steel, for example S235. So that the seal running thereon does not produce much friction and does not damage the shaft (race), the shaft is preferably hard-chromium-plated.

The circumferential ring preferably consists of steel having good magnetic conductivity or soft magnetic steel and is connected to the shaft in a rotationally fixed manner, in particular pressed.

The operating knob or the rotating unit is preferably connected to the shaft via a torque transmission element, for example a square with a slot. The operating knob or the rotating unit is braced without play by the torque transmission element (for example screwing using a countersunk screw).

In preferred developments and configurations, at least one control device is provided, the control device being suitable and designed to dynamically control the magnetic field generation device. The magnetic field from the magnetic field generation device is preferably dynamically generated on the basis of a rotational angle in order to provide a dynamic or adaptive and angle-dependent haptic latching pattern. In this case, it is particularly preferred for the haptic operating device to comprise the control device. The rotational angle can be derived from a relative or absolute angle position. It is also possible for an angle change to be used as the rotational angle.

Such configurations are very advantageous since latching points at which the rotating unit practically engages can be dynamically provided over one or more angular ranges. It is also possible to dynamically generate end stops at which the torque needed for further rotation is considerably increased above a particular rotational angle in one direction of rotation or the other.

A control device is preferably provided and the control device is designed to accordingly rotate a representation of contents of the display device in the opposite direction on the basis of a signal from the sensor or angle sensor. Such a configuration is advantageous, in particular, in the case of a co-rotating display unit since the orientation of the represented contents is left substantially unchanged. For this purpose, the representation of the contents of the display unit can be rotated precisely by the same amount in the opposite direction by which the rotating unit is rotated. It is also possible for the rotation in the opposite direction to be carried out only to a certain extent. In these configurations, the represented contents on the display unit can remain substantially unchanged or even completely unchanged during rotation of the rotating unit.

The contents of the display unit can also be changed in a manner corresponding to the operator's viewing position. If the rotating unit or the operating element is operated, for example, by the driver in a motor vehicle, the display contents or the angle of the display contents is/are oriented toward the driver (for example in the 8 o'clock position). If the operating element is actuated by the front-seat passenger, the display contents are accordingly oriented, that is to say in the 4 o'clock position, for example. The haptic latching pattern or the latching positions is/are also adapted in association with this.

In this case, the haptic latching pattern can also vary the haptic torque. This is advantageous because the driver will operate the operating element with his right hand and the front-seat passenger will operate the operating element with his left hand. For most people, the feeling in the hands differs and this can be counteracted. Therefore, the latching pattern or the latching torque or the latching torque profile can be individually adapted to the operator via the rotational angle.

The menu may be entirely different if, for example, children rotate it (they are identified using keys, a fingerprint in the cover, smartphone, smartwatch). In this case, only restricted operation may then be possible (for example no hot temperatures, machines: no high speeds etc.) or operation of more sensitive, other latching patterns may be possible.

In the case of machines in companies, for example processing machines, or in the case of copiers, the menu and the latching pattern can change according to the operator. A warning can also be given via the haptic knob, which can prevent operating errors, particularly with new operating personnel, for example.

At least one separate contact element is preferably arranged between the two components. Such a contact element is preferably in the form of a contact ring and is used, in particular, as a friction ring and may be in the form of an O-ring, for example. The friction ring is used as a rotating ring and is preferably at least in occasional contact with at least one component. The contact element may have, in particular, a round cross section or else preferably a flat, flattened or else rectangular cross section.

Such a contact element or such a contact ring or friction ring makes it possible to ensure reliable contact between the two components or rolling contact on one of the components. The contact ring is particularly preferably elastic and can be produced or formed, for example, from a rubber material or from a rubber-like material.

A channel is particularly preferably formed between the two components, and at least a plurality of rotating bodies are particularly preferably provided in the channel.

The contact element or the contact ring or at least one contact ring or friction ring or friction element is particularly preferably arranged in an intermediate space or internal space between the two components. In particular, the contact element is arranged or fastened in the channel between the two components. For example, the contact element or the contact ring may be arranged in a circumferential groove on one of the two components. It is also possible for a contact element or a contact ring to be respectively provided on both components. At least one rotating body is particularly preferably in contact with at least one contact element/contact ring.

It is also possible for at least one rotating body to be equipped with at least one contact element or contact ring. For example, all or substantially all rotating bodies may each be provided with a contact element or contact ring. The contact ring may have any desired shape, for example a quad ring or a rectangular ring, without being restricted thereto.

The contact elements/contact rings between the components and/or the rotating bodies and the components ensure reliable contact between the contact element/contact ring and the two components, thus ensuring that, in the case of a relative rotation of the two components with respect to one another, the rotating body co-rotates at least for most of the time.

Such a configuration is particularly advantageous if the intention is to use the wedge effect for wedging magnetorheological particles.

A configuration without the use of (flexible) contact elements or contact rings enables even lower base friction and is therefore particularly preferred.

The basic body preferably comprises a base plate and a holding housing, and a shaft is rotatably held on the holding housing. The magnetorheological medium is preferably held between the basic body and the shaft. For example, the magnetorheological medium may be held in an internal space of the holding housing.

rotating unit is preferably connected to the shaft in a rotationally fixed manner. The connection can be effected using a force fit and/or a form fit.

In advantageous configurations, the shaft is rotatably supported at one end on the base plate. In particular, the shaft is resiliently supported on the base plate using one end. This makes it possible to preload the shaft in a defined position.

The basic body and the shaft preferably each have a circumferential running surface for the rotating bodies adjacent to the base plate. The running surface(s) may be provided on a cylindrical, convex or concave or else conical circumferential surface.

At least one running surface preferably has at least one circumferential groove for the rotating bodies and/or for at least one contact element or at least one contact ring. This ensures that the contact ring and the rotating bodies assume a defined position.

In advantageous configurations, the running surface of the shaft is formed on a circumferential ring with an increased diameter. In preferred developments, a holding space, in particular an annular holding space, in which an electrical coil is arranged as the magnetic field generation device, is formed in the holding housing. In all configurations, the electrical coil may also be arranged at other locations or at or in other forms of recesses.

The electrical coil is preferably arranged substantially axially adjacent to the rotating bodies. This makes it possible to ensure that the magnetic field generated by the electrical coil acts, to a high degree, on the rotating bodies or the channel and the magnetorheological medium contained in the latter.

The circumferential ring is preferably separated, on an end face, from an end face of the holding housing by a gap. A free axial distance in the gap is preferably considerably shorter than a free radial distance at the channel. The free radial distance at the channel results from the radial distance between the two components and, in particular, from the free radial distance between the circumferential ring and the end face or running surface in the holding housing. In particular, the end face is an axial surface but may also be part of a lateral surface of a cone. A ratio of the free axial distance to the free radial distance is preferably less than 1 to 2 and, in particular, less than 1 to 5 and preferably less than 1 to 10.

In preferred configurations, the holding housing and the circumferential ring consist substantially or completely of a material with better magnetic conductivity than the base plate. This makes it possible to ensure an effective flux of the magnetic field.

The actuation sensor preferably senses a distance or a measure of a distance between the basic body and the rotating unit.

In all configurations, it is preferred for a free distance between the rotating body and the component or at least one component to be at least twice as large as a typical average diameter of the magnetically polarizable particles in the magnetorheological medium. At least one region containing the magnetorheological medium is preferably provided between the rotating body and at least one component, the magnetic field from the magnetic field generation device being able to be applied to said region in order to selectively concatenate the particles and/or wedge them with the rotating body and/or release them.

The region which contains the magnetorheological medium and at which the particles selectively concatenate and/or wedge with the rotating body has an acute angle, in particular, in the activated state.

It is also possible for the magnetorheological particles to be concatenated in the channel without using rotating bodies.

If rotating bodies are used, the region, in particular the acute-angled region, between the rotating body and a component preferably tapers in the direction of the relative movement of the component relative to the rotating body.

In particular, the two components can be coupled to one another selectively and in a controlled manner.

In the sense of this application, the term "coupling intensity" is understood as meaning the coupling force and/or the coupling torque between the two components. If linear force transmission is desired, for example, the coupling intensity corresponds to the coupling force. If a torque is intended to be transmitted, the coupling intensity is used to mean the coupling torque.

The viscosity of the magnetorheological medium can preferably be changed by the field, as a result of which it is possible to influence the displacement work needed for the relative movement of the components and/or rotating bodies which can be moved relative to one another.

Displacement work is also understood as meaning the displacement force needed to displace the medium during a relative movement.

A considerable and surprising advantage of the magnetorheological transmission apparatus used results from the considerably intensified effect of the magnetic field from the magnetic field generation device in the channel. The acute-angled region containing the medium acts as a lever and therefore virtually like a strong mechanical lever transmission, the lever considerably intensifying the effect of the magnetic field by a multiple. As a result, either the field strength of the magnetic field generation device can be reduced with an effect which remains the same or else the effect of the magnetic field is intensified with a field strength which remains the same or the effect is even considerably increased with a reduced field strength. The acute-angled region containing the medium increases the effect by a multiple, in particular, if the magnetic field acts on the medium. In particular, the magnetic field acts at least occasionally on the acute-angled region which contains the magnetorheological medium or is formed.

As a result of the fact that the rotating body is arranged at a considerable free distance from the at least one component, a macroscopic wedge which can be used to transmit strong clutch or braking torques can be produced. Considerable construction volume can be saved as a result of the completely surprising multiplication of the effect. The effect used is based on the wedge formation (cluster formation) and not only the magnetorheological concatenation of individual particles. The typical reaction time for the wedge formation requires several milliseconds, while individual particles are concatenated according to the MRF effect already within approximately 1 millisecond. This time duration, which is multiple times longer, is due to the wedge formation. Such a considerable intensification of the effect was not expected. The longer reaction time of, for example, 5, 10, or 20 milliseconds is more than sufficient in many applications.

The channel can also be an intermediate space or a space which is open on four sides.

An acute-angled region of the channel is defined as that channel region which appears approximately to have an acute angle in at least one cross section through the shape of the rotating body and components. The sides of the region do not have to be straight and can also be curved and/or have another contour. The acute-angled region defines that part of the channel in which the rotating body and components are at the shortest distance from one another, in particular, or touch, and the adjoining region, in which the surfaces of the rotating body and components move away from one another.

Under the effect of a magnetic field, the acute-angled region containing the magnetorheological medium is formed, in which a considerably increased viscosity is present.

A good torque to weight ratio, which can be greater than 100 Nm/kg, is possible.

A rotating body is preferably set into a rotational movement by a relative velocity in relation to at least one component. It is possible for the circumferential velocity of the rotating body to be equal to the relative velocity in relation to the component. However, it is also possible for the circumferential velocity of the rotating body on its outer surface to be greater than or less than the relative velocity. In particular, it is possible for the circumferential velocity of the rotating body on its outer surface to be less than the relative velocity of the rotating body in relation to the component.

The rotating body can be designed to be substantially rotationally symmetrical around at least one axis of rotation. It is likewise possible for the rotating body to be designed to be rotationally symmetrical around a plurality of axes of rotation. For example, the rotating body can be in the form of a sphere or ellipsoid. It is also possible for the rotating body to be in the form of a cylinder, roller, or generally a rolling body. In particular, an approximately cylindrical configuration has proven to be advantageous since, in the case of a cylindrical rotating body, for example, the acute-angled region containing the medium forms over the entire width of the rotating body and is thus substantially wedge-shaped. In these and other configurations, the acute-angled region has a wedge shape.

However, it is not necessary for the rotating body to be rotationally symmetrical. Rotating bodies having elliptical or egg-shaped cross sections or rotating bodies having indentations like golf balls or having regular or irregular indentations and/or protrusions can also advantageously be used. The surface of the rotating bodies can be smooth, but does not have to be. Since the rotating bodies are not used to mount and support the components relative to one another, a symmetrical and/or smooth surface is not necessary. Rotating bodies having a rough and/or irregular surface can even be advantageous since the wedge effect is intensified. Increased wear does not occur since the rotating bodies are not used for mounting and transmitting load-bearing forces.

The effect is preferably not intensified solely due to intensification or bundling of the magnetic field, but rather above all also due to the particles clustered in front of the rotating bodies or rollers and the compaction thereof. Owing to the magnetic field, the particles cannot move away and thus compact more rapidly to form a wedge. The wedge can be externally controlled easily via switch. The advantage in the case of magnetorheological fluids such as MRF is that the wedge can disengage again by canceling the magnetic field. The wedge can be influenced using the magnetic field—without mechanical movement or force introduction. It has proven to be advantageous for targeted influencing and reliable control that the free distance between the rotating body and the component is greater than a multiple of the particle diameter.

The diameter of the particles of the magnetorheological medium is between 1 µm and 10 µm, in particular. The typical mean diameter of the particles of the magnetorheological medium is the arithmetically averaged diameter of the particles which are larger than the smallest percent and which are smaller than the largest percent. As a rule, this value corresponds to the mean value of the diameters of the largest and the smallest particle, that is to say 5.5 µm in the selected example. If, however, for example, a very small number of even smaller particles are present, this does not change the typical mean diameter thus determined. The same applies if, for example, individual particles having a diameter of 10.5 µm or 11 µm are to be included.

The free distance between the rotating body and the component is preferably greater than 30 µm and, in particular, less than 300 µm. The typical mean diameter of the particles is preferably between 3 µm and 7 µm. The free distance between the rotating body and the component is preferably greater than 70 µm and, in particular, less than 250 µm.

The acute-angled region advantageously wedges the two components, which are freely movable relative to one another without a magnetic field, upon application of a magnetic field. A mechanical wedge in the form of a separate fixed part is not required for this purpose.

The acute-angled region is preferably provided between the body and one component in such a manner that the acute-angled region tapers in the direction of the relative movement of the component relative to the rotating body. If a cylindrical rotating body rolls on a flat surface of one component, the acute-angled region forms in a wedge shape in front of the rotating body. A wedge which is concatenated as a whole and inhibits the relative movement of the rotating body to the component arises due to the concatenation of the particles in the medium.

The rotating body and, in particular, each rotating body is particularly preferably in the form of a separate part between the first and second components. It is then preferred for one component, as the outer component, to surround the other component, as the inner component. For example, a (drive) shaft can be provided as the inner component. The other or outer component can be used for braking, for example, and can radially surround the shaft. The rotating bodies can be provided between the shaft and the outer component. It has been shown that rotating bodies which rotate around their own axis are considerably better for achieving the wedge effect. Finished bearing shells are not necessary. The transmission of a clutch or braking torque functions independently of the quality of the rolling surfaces.

At least one separate bearing or roller bearing is provided for mounting the two components. The rotating bodies ensure, with the wedge effect, the transmission of the desired torques, while the roller bearing or bearings ensure(s) the defined guiding and support of the two components and the uniform running gap.

A transmission may also be arranged or kinematic levers can be used between the drive shaft and the rotating body or between the rotating body and the basic body/housing. As a result, the torque and the rotational angle can be varied in a wider range or the haptic operating knob can have a smaller construction and the construction volume can therefore be considerably reduced. The transmission may be in accordance with the prior art, preferably a planetary transmission or harmonic drive which is free of play as far as possible.

In all configurations, the free distance is preferably at least twice, five times and, in particular, ten times as great as the largest typical particle diameter. In specific configurations, a free distance of between approximately five times and, in particular, ten times and twenty times the largest typical particle diameter has proven to be advantageous. In the case of larger free distances, the maximum transmittable torque is reduced again since the wedge effect subsides. In the event of excessively short free distances, a blockade can occur even without a magnetic field. In addition, disengagement of the wedge after the shutdown of the magnetic field then cannot always be ensured.

The mean particle diameter is understood as meaning the arithmetic mean of minimum and maximum particle diameters. Most MRF have magnetically polarizable particles which have a size distribution of between approximately 1 µm and 10 µm. The mean particle diameter is 5.5 µm in this example. In the case of variable size distributions, the largest typical particle diameter is understood as meaning a particle diameter which is exceeded by only fewer than 1% of the particles. The largest typical particle diameter is somewhat less than 10 µm in the mentioned example, so that 10 µm can be presumed to be the largest typical particle diameter here.

The free distance is preferably greater than 1/500 and preferably greater than 1/250 and, in particular, greater than 1/100 and particularly preferably greater than 1/50 of a diameter of at least one rotating body, and, in particular, the free distance is less than 1/10 and, in particular, less than 1/20 of the diameter of the rotating body.

The free distance is preferably greater than 1/300 of the external diameter of the inner component and/or greater than 1/500 of the internal diameter of the outer component. The free distance is preferably greater than 30 µm and in particular less than 200 µm.

Variations by +/−20% are preferably possible in the case of all numeric specifications. A particle is understood below as meaning a magnetically polarizable particle.

If oversized rotating bodies and/or shaft diameters are used, other distances can be advantageous. An advantage of this magnetorheological transmission apparatus having at least two components which can be coupled is that the wedge formation is manufacturing tolerant, that is to say, for example, manufacturing-related and installation-related differences in gap heights, surfaces, dimensions and also thermal expansions or load-related shifts of components have a minor influence thereon and cause negligible torque or force differences.

For example, a structurally related change of the gap within certain system limits can also be detected by sensors and worked out by field adaptation, for example.

In preferred configurations, the rotating body is part of the first or the second component. This means that the rotating body, which is in the form of a rotating body, for example, is part of the first component and rolls on the second component, for example. The rotating body can also be without mechanical connection to both components, however.

In the acute-angled region, which is wedge-shaped, for example, the ferromagnetic particles concatenate in the medium upon application of an external magnetic field and result in a locally more solid structure which opposes the further relative movement between the rotating body and the adjacent component. The particles in the wedge-shaped part can be additionally compacted in the direction of movement in front of the rotating body by the rolling movement of the rotating body. However, depending on the design of the rotating body, this compaction can also be performed by pitching, tilting, or other movements relative to a component.

For example, if the rotating body rolls on the surface of one component and such an acute-angled region forms in front of the rotating body, particles in the medium are entrained and set into rotational movement by the outer surface due to the rotational movement of the rotating body, but the hardening acute-angled region strongly opposes such a rotational movement. The acute-angled region in wedge shape results in a force on the rotating body away from the component. Such a force and a movement resulting therefrom can optionally also be used for fine adjustment purposes. A rotational movement can preferably be converted into an axial displacement of the rotating body by the acute-angled region in wedge shape when the magnetic field is activated. The rotating body is thus virtually caused to float by the particles. It is also possible to provide the rotating body or a component with thread-shaped notches, for example, or to mount them at an incline relative to one another, in order to change the effective direction of the resulting force or to further increase the achievable force transmission. A linear movement can thus be converted into a rotational movement using a type of threaded rod. The relative movement is inhibited by applying a field.

It is likewise preferred for the rotating body to be in the form of a separate part between the first component and the second component. Such a configuration can be particularly advantageous since two acute-angled regions or wedge-shaped regions can occur between the rotating body and the two components. If the rotating body practically rests against the first component on one side and practically rests against the second component on the other side, acute-angled regions which are subjected to the magnetic field from the magnetic field generation device form on both sides. The effect is thus increased. It is not necessary for this purpose for the rotating body to rest completely against the first component or the second component. A small gap remains between the rotating body and the respective component. The size of the gap is dependent, inter alia, on the properties of the medium. In particular, the size of the gap can be at least five times and preferably at least ten times or twenty times a typical or mean particle diameter.

The ferromagnetic particles consist, in particular, of carbonyl iron powder. The fluid can be an oil, for example.

It is also possible for magnetorheological and electrorheological media to be used jointly. The use of other media which are influenced and concatenated, for example, by corresponding fields is also conceivable. It is likewise possible to use media which change their rheological properties depending on other physical variables such as temperature or shear velocity.

The channel can be completely or also only partially filled with the medium. At least the acute-angled region of the channel is preferably filled with the medium.

In all configurations, the first and/or second component can be rotationally symmetric. For example, the components can each be in the form of plates or cylindrical bodies, between which rotating bodies are provided, in order to increase the effect of the magnetic field from the magnetic field generation device accordingly through the wedge effect.

In all configurations, it is preferred for the magnetic field to run through the rotating body and, in particular, substantially transversely to the relative movement of the components relative to one another and from one component to the other component at least partially through the rotating body. Such a configuration has proven to be particularly effective since the effect of the magnetic field at the transition points from the rotating body to the walls of the channel is particularly strong. Depending on the acting magnetic field, it is therefore advantageous if the rotating body is at least partially magnetically conductive. In particular, at least one component and in particular both components and/or the at least one rotating body is/are made at least partially of a ferromagnetic material. The relative permeability is preferably greater than 500. The relative permeability of the material can also be 1000, 2000, or more. Rotating bodies made of a ferromagnetic steel, such as ST37, are possible, for example.

The material can be demagnetized by a damped magnetic alternating field, so that a lower base torque is achieved without a residual field.

In all configurations, it is preferred for the magnetic field generation device to comprise at least one permanent magnet and/or at least one coil. It is also possible to use one or more permanent magnets and one or more electrical coils.

It is possible and preferred to permanently change the magnetization of the permanent magnet by means of at least one magnetic pulse from an electrical coil. In such a configuration, the permanent magnet is influenced by magnetic pulses from the coil such that the field strength of the permanent magnet is permanently changed. The permanent magnetization of the permanent magnet can be set by means of the magnetic pulse from the magnetic field generation device to an arbitrary value between zero and the remanence of the permanent magnet. The polarity of the magnetization is also variable. A magnetic pulse for setting a magnetization of the permanent magnet is, in particular, shorter than 1 minute and preferably shorter than 1 second and the length of the pulse is particularly preferably less than 10 milliseconds.

As an effect of a pulse, the shape and strength of the magnetic field are permanently maintained in the permanent magnet. The strength and shape of the magnetic field can be changed by means of at least one magnetic pulse from the magnetic field generation device. The permanent magnet can be demagnetized by a damped magnetic alternating field.

AlNiCo, for example, is suitable as a material for such a permanent magnet with variable magnetization, but other materials having comparable magnetic properties may also be used. In addition, it is possible to produce the entire magnetic circuit or parts thereof from a steel alloy with strong residual magnetism (high remanence) instead of a permanent magnet.

It is possible to use the permanent magnet to generate a permanent static magnetic field which can have a dynamic magnetic field from the coil superimposed on it in order to set the desired field strength. The current value of the field strength can be varied arbitrarily by the magnetic field from the coil. It is also possible to use two separately controllable coils.

In all configurations, it is preferred to provide at least one control device. It is also possible to use an energy store, for example a capacitor, to store at least a fraction of the required energy. At least one sensor or a plurality of sensors can be used to detect relevant data, for example the relative velocity of the components in relation to one another or the prevailing field strength and the like. It is also possible to use a temperature sensor as the sensor, which triggers an alarm if predetermined temperature conditions are exceeded, for example. A rotational angle encoder can advantageously be used to have data relating to the angle position of the components in relation to one another at any time.

In all configurations, it is preferred that the permanent magnet at least partially consists of a hard magnetic material whose coercive field strength is greater than 1 kA/m and, in particular, greater than 5 kA/m and preferably greater than 10 kA/m.

The permanent magnet can at least partially consist of a material which has a coercive field strength of less than 1000 kA/m and preferably less than 500 kA/m and particularly preferably less than 100 kA/m.

The magnetorheological transmission apparatus is part of an operating device which comprises, in particular, an operating or control knob or the like.

The rotating body and at least one component can touch at at least one point or on at least one line. It is possible and preferred for the rotating body to be at rest relative to at least one component.

The rotating body can preferably move relative to at least one component, for example in the form of a rotational or tilting movement.

The field strength can have a strong gradient depending on the respective distance between the rotating body and components.

The field strength preferably increases in the acute-angled region between the rotating body and components toward the region having the shortest distance.

The need for maintenance is low since few and simple parts are used. If necessary, the maintenance can be carried out by simply replacing the magnetorheological fluid. The structure is simple and robust and power feedthroughs are not required. In addition, the energy requirement is lower than in the prior art because the wedge effect substantially contributes to influencing the relative movement of the components. It is possible to achieve a torque/weight ratio of >100 Nm/kg.

In magnetorheological clutches or brakes without a wedge effect, the magnetic field poles move relative to one another and generate shear forces (direct shear mode) in the interposed MR fluid. The shear forces vary depending on the magnetic field. No magnetic field means no or low shear forces (no chain formation in the MRF), maximum magnetic field means maximum shear forces and therefore maximum braking force or braking torque. In simplified form, the magnetic field and shear forces are proportional.

In the present invention, through appropriate design of the individual components, dimensioning, and field introduction, a very advantageous behavior which deviates therefrom can be provided. This advantageous behavior is expressed in that a substantially lower magnetic field, and therefore a lower current intensity, is needed to maintain the acute-angled embodiment or the MR fluid wedge than is needed for the initial generation of the wedge. This is because the particle cluster no longer falls apart so easily once it has first been accumulated and has been quasi-mechanically compacted by the special movements fundamental to this invention under the influence of a correctly introduced magnetic field. As a result, for example, after a corresponding time for achieving this state, a braking torque can be maintained using the fraction of the magnetic field or electrical power (coil current), which is advantageous in terms of energy.

If clutches having magnetorheological fluids according to the prior art are loaded beyond the maximum transmittable clutch torque, individual particle chains begin to break apart, whereby slip or slipping through results. The maximum clutch torque is maintained, however, or sometimes even slightly increases, and the clutch does not disengage. Depending on the application, this can be undesirable, for example if a drill bit of a drill jams during drilling.

In the present invention, through appropriate design of the individual components, dimensioning, and field introduction, a very advantageous behavior which deviates therefrom can be provided. This advantageous behavior is expressed in that, if a maximum force is exceeded between the moving parts, the wedge (material cluster) generated by the magnetic field is suddenly pressed through the gap (material displaced) and the force decreases suddenly at the same time. On account of the relative movement resulting therefrom and the high applied force, a new wedge does not form, as a result of which the relative force remains low. In the case of overload clutches, this behavior is very advantageous. The maximum force (triggering force) or the maximum torque (triggering torque) can be preset via the magnetic field.

Furthermore, demixing, sedimentation, and centrifugal force problems are reliably avoided since continuous mixing of the particles in the medium is achieved by the rotating bodies which are rotating.

On account of the substantially higher transmittable torques and forces, it is possible to implement clutches, brakes or the like having substantially smaller diameters. On account of the low MRF channel height and the rotational movement of the rotating bodies, demixing is practically not relevant in the case of the present invention.

The invention can be used in manifold ways. Use as an operating element on domestic appliances such as washing machines and also to choose the operating state of vehicles is possible.

The invention can also be used in the case of a three-dimensional movement. The rotation and pendulum movement can thus be restricted or blocked by the MRF wedge. The acting torque is continuously adjustable and switching times in the range of a few milliseconds can be achieved. The structure is simple and no mechanically moving parts are required for varying the torque. A further advantage is that almost noiseless operation is possible. The additional costs are low and a magnetorheological transmission apparatus according to the invention can be designed to be operationally reliable if, for example, a permanent magnet with remanence is used to set a magnetic field. The wedge effect enormously intensifies the effect, with the result that a smaller installation space is achievable.

In all configurations, the rotating bodies do not have to be smooth, but rather can have rough or uneven surfaces.

The haptic operating device can be used in manifold ways and comprises, for example, controllers for crane operation or the like. In this case, the rotation can be controlled more stiffly, depending on the load. It can also be controlled on the basis of the load height.

The use in "force feedback" applications or in "steer by wire" applications, such as in the steering wheel, gas pedal or brake pedal, is also of interest. The use on operating elements in vehicles, steering wheels, automobile radios, windshield wiper switches, home appliances, stereo systems, remote controls, cameras, test stands, oscilloscopes, operating apparatuses, robot controllers, drone controllers and when positioning military weapons etc., is also possible.

In all configurations, it is also possible to use magnetic seals to seal an apparatus according to the invention, in addition to a seal with a sealing lip. The seal can be produced via a permanent magnet here. Advantages of such a configuration are smaller base forces, freedom from wear, and the permissibility of greater manufacturing tolerances. In addition, there is a defined overload behavior since a defined breakthrough occurs if the overload is exceeded. It is possible to use such a seal in front of or behind an apparatus according to the invention or to use it in front and behind.

A significant advantage of the magnetic seal is the very low friction; however, it can be necessary to use yet another seal since such a seal possibly only holds back MRF particles and allows oil as the base fluid to pass through the gap over time, for example. Therefore, such a magnetic seal can be used as an outer seal in order to hold back MRF particles. A further seal, for example a conventional seal, then only seals off the carrier medium.

A movement of the magnet can be used to achieve lubrication in the MRF, as well as material transport and cooling, for example via hydrodynamic effects. In addition, a flow away from the seal can be achieved and pressure differences can be dissipated.

In order to set the play between two parts, for example, or to remove play from a design and to compensate for manufacturing tolerances, for example, it is possible to use a force or an axial force and/or a radial force which is caused by an MRF wedge effect.

In all configurations, it is preferred to provide a settable permanent magnetic field strength via remanence. In preferred embodiments, a bearing having a magnetorheological transmission apparatus according to the invention has no or only minimal residual magnetism (remanence) itself. Otherwise, a position-dependent counterforce of different strength can occur since the parts move in relation to one another.

In advantageous configurations, the remanence material should be arranged in a general region of the bearing which is permeated, in particular, by the magnetic field in a position-independent manner, thus, for example, the inner shaft or the outer shell etc.

However, it is also preferred to use the effect of the position-dependent magnetization by using, for example, the inner running surface having remanence in order to generate specific latching torques, for example. This can be performed, for example, for haptic feedback about variable latching torques with respect to their strength, the rotational angle, or the end stop or the like. Not all bearing balls have to be ferromagnetic, depending on the desired setting capability.

It is also possible to provide a magnetorheological transmission apparatus having a design deviating from the conventional bearing structure. For example, the direction of the magnetic field can also be oriented at least partially or completely approximately parallel to the axis. At least partial orientation parallel to the rotational direction or movement direction or in the tangential direction is also possible. It is also possible for the entire magnetic circuit to be arranged nearly or completely in the interior or on the end face.

The material of the magnetorheological transmission apparatus does not have to be completely ferromagnetic; depending on the desired application or magnetization, it can be advantageous if individual parts of the magnetorheological transmission apparatus are not ferromagnetic or are only partially ferromagnetic.

Depending on the application, it is also conceivable to manufacture at least one part from different materials, to obtain locally differing magnetic properties.

The haptic operating device preferably functions with a magnetorheological transmission apparatus with a wedge effect. The position or the rotational angle of the rotary knob can be determined via the rotary encoder and the rotational resistance can be varied in a wide range. Thus, for example, a haptic interface with variable latching torques and arbitrarily settable end stop can be constructed, which changes its properties depending on the currently selected menu. A low or high torque and/or a small or large latching pattern/ripple and also a variable latching pattern—depending on the menu to be operated—can be set. The profile of the torque increase and decrease can be set or varied depending on the situation, for example as a square-wave, sinusoidal, sawtooth, or arbitrary profile. A stop can also be simulated. The stop can be hard or can have a predefined or situation-dependent torque profile. The torque profile can be different during rotation in one direction than during rotation in the other direction.

The rotary knob as one component is preferably fixedly connected to the shaft as the other component which is in turn rotatably mounted in the housing. The relative movement or relative position is detected via a rotary encoder, for example via a magnetic, optical or (via buttons) mechanical incremental encoder. A potentiometer with sliding contacts can also be used, but only specific rotational angles are usually permissible using said potentiometer.

A sealing ring is advantageous so that the magnetorheological fluid remains in the housing. The seal can also only consist of permanent magnets or a combination of a permanent magnet and a conventional seal.

The inner region, i.e. the volume enclosed by the seal and housing, is at least partially filled with a magnetorheological fluid.

The housing is preferably designed as a pot, i.e. it is closed on one side. Only one sealing ring is thus required. A continuous shaft (two-sided shaft) is also conceivable.

The coil can generate a magnetic field, wherein the magnetic circuit is closed via the housing, the shaft, and the magnetorheological transmission apparatus. The magnetic field required for the wedge effect can thus build up in the magnetorheological transmission apparatus. The coil is advantageously fixedly connected to the housing, which makes the cable routing easier.

The structure is robust and can be designed such that almost no magnetic stray fields are generated outside the housing. However, many other structure variants are conceivable, which can have specific advantages depending on the application.

For example, the coil can also be arranged outside the housing, the magnetic field then acting on the magnetorheological transmission apparatus through the housing. No mechanical connection is necessary here between the coil and the housing; the coupling of the magnetic circuits is sufficient to influence the magnetorheological transmission apparatus in the housing. In particular, the coil does not have to be permanently on or in proximity to the housing and can be designed such that it can be removed from the housing as a separate unit. Permanent magnets can also be provided in the magnetic circuit.

In a preferred embodiment, the rotary knob can be electromagnetically driven, for example, and can also actively exert a force (force feedback) in order to be able to statically generate a specific countertorque. In this design, a better torque to installation space ratio is achieved than in many designs according to the prior art. In addition, the production costs are low because of the simple structure since, for example, the rolling surfaces of the components do not have to be highly precise in haptic applications and also generally do not have to withstand high speeds and a large number of revolutions. In general, the magnetorheological transmission apparatus described here has a very low base friction (OFF state). A battery and a control command transmission unit (radio, WLAN, Bluetooth, NFC, antenna) are preferably also integrated in the actuator or rotary knob. The haptic knob can then be placed anywhere and does not require a wired control connection or current connection. The MRF wedge principle requires very little current (power) in relation to the torque. It is therefore also highly suitable for battery operation or for wireless energy supply. Both the required energy and control commands and also, for example, measured values from sensors such as rotational angles can be transmitted wirelessly.

A preferred embodiment manages without a battery and receives the energy required for the function by means of inductive coupling. Embodiments which acquire the energy required for operation directly from the environment and buffer it locally (energy harvesting) are also particularly preferred. Thermoelectric generators, solar cells, elements which convert vibrational energy into electrical energy, and others, as well as corresponding local energy stores are possible for the energy conversion. It is also conceivable to use the movement of the magnetorheological transmission apparatus itself to generate energy.

If a magnetic field is applied to the magnetorheological transmission apparatus at least partially via a permanent magnet, and the magnetization of the magnetic field is permanently changed by at least one magnetic pulse from at least one electrical coil, several advantages result. In specific cases, weight and space advantages can be achieved, for example by using the remanence and the pulsed operation of a coil which does not always have to be energized. The wires of the coil can be dimensioned to be thinner and lighter because they are each energized only for a short operating time. This can result in advantages in the case of weight, power demand, space requirement, and costs.

Therefore, it can be advantageous in specific applications that, due to the pulsed operation of the electrical coil, it can be significantly smaller than if it must be designed for a switched-on duration of 100%. The heating of the coil usually does not play a role in pulsed operation since short-term power loss peaks are buffered by the intrinsic heat capacity of the coil and the parts surrounding the coil. Very high current densities in the turns can thus be tolerated or thinner lines can be used, as long as the mean power loss remains acceptable over longer periods of time.

In the case of a smaller coil, the magnetic circuit surrounding the coil can also usually be smaller, which is why a comparatively large amount of installation space, material, weight, and costs can be saved. Only the energy expenditure for a single pulse increases here, but this can be very well tolerated depending on the application. Overall, a large amount of energy can nonetheless be saved in comparison with a continuously energized coil.

In all configurations, it can be possible to supply the power in a wireless manner. The power can be supplied, for example, from the current source to the power electronics or from the power electronics to the coil via electrical, magnetic, or electromagnetic coupling, for example a radio link. When used in a bicycle, the power can be supplied externally via a docking station, for example. It is also possible to supply energy to all loads (forks, rear shock absorbers, display) via an energy source on a bicycle, for example. The power can also be supplied similarly in the case of a ski boot, ski, mobile telephone, or to the sensors.

An energy supply via radio can possibly have worse efficiency than conventional wiring. In addition, the energy transmission and its range can be limited. However, such disadvantages do not interfere depending on the application. It is advantageous that no wear of the contacts occurs. The energy transmission is usually secure from polarity reversal and short-circuit-proof since only a limited power is present on the secondary side. Furthermore, cable breaks are not possible and the apparatus is more movable as a whole.

In such configurations, however, it is advantageous to buffer the energy for at least one pulse in a capacitor or energy store. The energy supply of the system can thus have a smaller power since short-term power peaks of a pulse are absorbed by the capacitor. In addition, a discontinuous or pulsed energy supply can also be used.

One possible expansion stage of the present invention is a fully autonomous system which is wirelessly supplied with energy. For example, use on a bicycle is conceivable, in which case the system is supplied with energy by at least one small magnet on a tire.

In general, arbitrary "energy harvesting" units can thus be used to supply energy, for example solar cells, thermoelectric generators, or piezoelectric crystals. Elements which convert vibrations into energy can thus also be used very advantageously for the supply.

An embodiment similar to that in an electric toothbrush is also conceivable, in which the energy is supplied by inductive coupling. For example, the rechargeable battery can be inductively charged, without damaged cables or corroded or soiled contacts obstructing the charging process. Energy can be transmitted over longer distances via magnetic resonance.

The power supply of the remanence pulse can be effected via induction, as in the case of electric toothbrushes. The combination of the MRF wedge principle with remanence is particularly power-saving and advantageous.

A loudspeaker or a noise generating unit can also be integrated or assigned. This is advantageous since the rotary knob as the MRF wedge knob is mechanically noiseless per se. Both the rotation without and also with a latching pattern and/or the virtual stops are noiseless per se. The generation of the MRF wedge for a torque increase or to generate a latching pattern is likewise noiseless per se. By means of the noise source, such as a loudspeaker or a piezoelectric loudspeaker, for example, clicking can be associated with the virtual latching pattern at each latching position. The type, volume and duration of the noise can be individually assigned, but can also be changed or turned off if the user wishes.

Therefore, the torque, the latching pattern, the stops and the noise are programmable or adaptive. The noises can also be generated via external loudspeakers, for example standard loudspeakers in the automobile or the loudspeakers of the hi-fi system in the home.

The haptic knob can therefore practically replace the mouse wheel of a computer mouse. In the case of the latching pattern, not only the angular distance of the latching pattern can be settable, but rather also its profile shape, thickness etc. A latching pattern characteristic curve can therefore more or less be predefined.

The haptic rotary knob can also be mounted on an operating surface or on a screen. So that the display does not have to be removed for fastening the knob, it can consist of an upper part on the display and a lower part below the display. Data transmission via induction or the like, for example, is preferably provided. The display can thus be produced more cheaply as a surface.

It is also possible for an MRF haptic knob to also be pressed. The pressing can also act through an MRF whose properties are variable via a magnetic field.

The screen displays the information to be set which changes depending on the application. The function of the haptic knob is adapted thereto. In one case, adjustment is made by means of a latching pattern (for example setting the volume; a volume scale which can also have a logarithmic scale appears on the display).

In another case, adjustment can be made between two positions without a latching pattern, but with variable torque, thus, for example, between the 8:00 position and the 16:00 position or between the 4:00 position and the 8:00 position, in which case an increasing torque can be provided in each case before the end position. The latching pattern can also be used to approach defined positions, for example if a name input is requested.

The display can also be in the form of a touchscreen. Menu items can thus be rapidly selected and fine adjustments can be made by means of the rotating actuator. For example, it is not desirable in the case of automobiles to control the volume of the radio via touchscreen since the driver would otherwise always have to look for a long time at what and where he is currently adjusting, which distracts him. He also finds the rotating actuator with a brief glance or without looking at it.

The haptic operating element can also be globally displaceable on guides or kinematic levers. The haptic operating element which has a very compact and low construction can therefore be mounted above a display, for example. Depending on the position of the haptic operating device above the display (almost like the mouse pointer of a screen mouse), the underlying menu is haptically and dynamically adapted.

The adjustment using a mechanical actuator is also simpler and safer than via a touch display when cycling, for example. This is also true, in particular, if the cyclist is wearing gloves, for example, whereby the operation of a touch display is difficult or even impossible.

A combination of a display or touch display and a mechanical rotating actuator with variable torque/latching pattern is also possible. Such input devices can also be advantageous outside the motor vehicle, thus, for example, in the case of controllers for industrial installations, remote controls for televisions or radio vehicles such as toy helicopters, for example, and on PCs and games consoles, and control consoles for military applications (drone aircraft, rockets).

It is also possible for a haptic rotary knob with a display to replace the current computer mouse.

It is possible for the rotary knob or the actuator to be countersunk in the normal state and to be extended only if needed.

It is also possible to embody such a structural unit as a slide controller, in particular in combination with a linear MRF wedge unit.

It is also possible to equip a magnetorheological transmission apparatus with one or more poles and one or more elevations. In all configurations, it is possible for elevations or the like, which protrude from one component in the direction of the other component, for example, to be provided between the two components of the magnetorheological transmission apparatus.

Such a configuration is possible and preferred both in the case of rotational mobility and in the case of linear mobility of the two components with respect to one another.

Only one elevation can be provided or a plurality of elevations can be provided. It is possible for a ball or a roller or another rotating body to be arranged on at least one elevation and to be at least partially accommodated by the elevation.

If elevations are provided on one component, it is preferred for at least one pole or at least one magnetization unit or at least one magnet or one coil to be provided on the other component. The number of magnetization units or poles can be 1 or else greater.

The shape of the elevations can fundamentally be arbitrary and can be semicircular, pointed or blunt, for example. The holding region of rotating bodies is preferably accordingly rounded.

One or more magnetization units or poles can be in the form of an electrical coil plus core or a permanent magnet or can consist of remanence material or a combination thereof.

The distances between individual elevations and/or magnetization units are preferably approximately uniform, but can also be arbitrary.

The depth, i.e. the radial extent or the axial extent, of individual elevations or magnetization units with respect to others can be different.

The field strength which is applied to or acts on the individual magnetization units can, in particular, also vary at the same time.

The speed of the rotating bodies does not have to be equal to the rolling speed, and can also deviate therefrom, for example by step-down or step-up transmissions. The inner part which is formed by the elevations, for example in the shape of a star, can be mounted off-center to the outer part.

Such a magnetorheological transmission apparatus can be used, for example, as a haptic knob with a latching pattern or in furniture and drawer guides with positions.

The magnet or each magnetization unit or the inner part and/or the outer part can also consist of remanence material.

Since magnetorheological fluids concatenate very rapidly upon the application of a magnetic field, it can be sufficient in the normal state, for example when driving an automobile, if the magnetic field is turned off. It is generally entirely sufficient to only turn on the field when a first rotational angle change is initiated. A significant amount of energy can thus be saved.

Alternatively, a base torque can be implemented with remanence. When a rotational angle change is registered, a dynamic magnetic field can be built up, which can also pulsate to generate a virtual latching pattern.

In configurations in which the remanence is utilized, the magnetic field for the remagnetization can be externally applied. A corresponding coil, which acts through a cylinder, for example, can be used for the remagnetization.

The method according to the invention is used to operate technical equipment and devices and, in particular, vehicles and particularly preferably motor vehicles, a haptic operating device having a rotating unit being used and selectable menu items being displayed on a display unit, and a menu item being selected or chosen by rotating the rotating unit. In particular, a torque profile is dynamically changed during rotation of the rotating unit and/or the rotating unit latches at a number of haptically perceptible latching points during rotation, the number of haptically perceptible latching points then being dynamically changed, in particular during operation.

The method according to the invention has many advantages since it enables simple and dynamically adapted operation. The individual menu items can be selected by rotating the rotating unit and can be clearly haptically distinguished from one another since a latching point or a stronger rotational resistance can be felt at each individual menu item. As a result of the dynamically changing number of haptically perceptible latching points during operation, the operation of the operating device can be optimally adapted to the respective requirements and to current operating states of the technical equipment or of the vehicle. Such a dynamically adapted procedure is therefore not possible with the haptic operating knobs from the prior art and is not known from the latter.

The latching points are preferably generated by deliberately generating a magnetic field at a channel at least partially filled with a magnetorheological medium. Such a channel extends, in particular, between a basic body and a rotating unit which is rotated in order to actuate the haptic operating device.

An angular position of the rotating unit is preferably detected, and an intensity of the magnetic field is set on the basis of the detected angular position. In this case, the angular position of the rotating unit can be recorded in absolute or relative terms.

In preferred configurations, an end stop is dynamically generated in at least one direction of rotation. The magnetic field is particularly preferably set to be considerably stronger at the end stop than at a latching point. As a result of such a dynamically set end stop, an end stop can fundamentally be provided at any desired angle position, with the result that the complete rotational angle does not need to be used to arrive at an end stop. As a result, after relatively small rotational angles, a user can also be easily made aware of the fact that yet further menu items are not provided during further rotation. An end stop can thus be dynamically generated, for example, after 2, 3 or 4 latching points.

A latching point is preferably generated at a determined angle position by virtue of a stronger magnetic field being generated there or in the vicinity of the latching point than further away from the latching point. For example, a stronger magnetic field can be generated at angular locations adjacent to the determined angle position than at the angle position determined for the latching point.

It is possible for the magnetic field to be intensified during a rotational movement away from the latching point, with the result that the user can clearly feel the latching point.

It is possible and preferred for a relative local minimum of the magnetic field to be generated at a latching point, whereas relative maxima of the magnetic field are generated in the immediate vicinity of the latching point. The magnetic field can be reduced again further away from the latching point. This means that the magnetic field is intensified at a distance of up to 25% of the distance between two latching points, for example, whereas it is set to be relatively small at a latching point itself.

In preferred configurations, the angular distance between at least two adjacent latching points is dynamically set. For example, the angular distance between two latching points may be respectively 10 or 15° for a number of 4, 6, 8 or 10 latching points, whereas the angular distance may be increased to 30°, for example, in the case of only 2 latching points. The relative angular distance can fundamentally be increased for a smaller number of latching points, whereas the angular distance is decreased for a larger number of latching points.

However, it is also possible for an angular distance between two latching points to be decreased—to a certain degree—if fewer latching points are provided. For example, a relatively small angular distance of 15° or the like can also be selected in the case of only 2 latching points and therefore 2 menu items, whereas the angular distance may be 30° if 4 menu items are selected or 4 corresponding latching points are dynamically generated. The latching pattern spacing may also always be the same.

In all configurations, it is preferred for the rotating unit to be endlessly and/or freely rotatable in the switched-off state.

However, it is also possible for only a certain rotational angle of 150°, 180°, 360° or 720° or the like to be possible if, for example, there is a direct cable connection between a rotated part and a stationary part.

In all cases, it is also possible for a permanent magnet to ensure a certain base resistance during rotation in the switched-off state, for example. It is also possible to provide a mechanical or permanent-magnetic latching pattern for the switched-off state so that the user also receives haptic feedback in the switched-off state. In the case of a mechanical latching pattern, it is conceivable for the latter to be electronically compensated for in the normal operating state, with the result that, in the switched-off state, the user senses a mechanical latching pattern which is completely dynamically superimposed or replaced in the operating state.

In all configurations, it is preferred for the number of latching points to correspond to the number of currently available menu items. This means that, after selection of a menu item and appropriate guidance to a submenu, the number of then currently available latching points corresponds to the subitems in the then currently active submenu.

A selected menu item is preferably activated when the haptic operating device and/or the rotating unit is/are pressed. In all configurations, it is also possible and preferred for a touch-sensitive screen or a touch-sensitive display unit (for example capacitive, inductive etc.) to be used, in which a menu item can be selected by touching it with the finger or the like, for example. In all of these configurations, it is possible and preferred for both pressing of the haptic operating device and operation using the finger to be possible. This also applies to operation using gesture control. A gesture control sensor can be used additionally or instead of the screen for this purpose.

The display unit may be an LCD, TFT, IPS, Retina, Nova, White Magic, OLED, AMOLED or other screen type.

An associated method step is preferably carried out and/or an associated submenu is displayed and the number of latching points is dynamically adapted to the selectable menu items in the submenu when a menu item is activated.

A further method is used for operation or control in or of self-driving vehicles having an adaptive haptic operating device, the available menu items and the latching points of the operating device being adapted on the basis of an operating or driving state.

In this case, in particular, only those menu items or functions which are permissible based on the operating or driving state (in particular self-driving or are driven) can be selected and executed. Menu items and/or functions which possibly result in danger or are confusing are preferably hidden or deactivated.

Another method is used, in particular, for assisting with the rehabilitation of persons after illnesses, a haptic operating device being used. In this case, a variable rotational resistance is generated. In this case, the operating device can be used to open a door, turn a switch etc. The latching pattern and the force can be adapted in an infinitely variable manner.

In all variants, the haptic operating device has an infinite number of possible positions or latching patterns, in particular.

The combination of a touch display (display unit) plus a haptic operating device (haptic knob) can be used in a wide variety of applications. The same basic configuration (hardware) can be "adapted" by means of different software. For example, the operating device can be used in the washing machine as a rotating controller with coarse latching patterns (delicates, low-temperature, prewash etc.), and can be used in a baking oven with an infinitely variable, but increasingly difficult latching pattern for the purpose of adjusting the temperature. In all devices, the user therefore has a "known/identical" user interface but nevertheless product-specific user interfaces. The manufacturer hereby has more common parts, which makes everything more cost-effective.

Modern cameras have a large number of dials and operating knobs.

Depending on the program selected, corresponding fine adjustments (for example aperture stops etc. in this case) can be changed by means of the haptic rotating unit (rotary knob) by pressing on the display (or a knob). Adapted latching patterns or latching points can be used for aperture stops and programs. A zoom can be operated in an infinitely variable manner with a central position at a focal length of 50 mm and with stops at the end of the zoom. The actuation force may possibly be increased shortly before the end stop.

These cameras may also be controlled using a mobile telephone or the like. An operating device according to the invention is also advantageous here.

The haptic operating device may also be the program selection element at one time and then the adjusting element for the zoom, each with different latching patterns.

The haptic latching pattern may also be installed in the objective in the multifunction rotating ring of the housing (multifunction ring in the cameras). The latching pattern changes depending on the use of the ring (zoom, aperture stops, shutter speed etc.).

In order to save space, weight and costs, the entire ring need not be in the form of an MRF ring in this case, but rather may be controlled via a small haptic element according to the present invention which is located to the side and is operatively connected via toothing or the like.

Persons with impaired eyesight can be assisted by corresponding feedback from the haptic operating element, for example in the form of a Morse code.

A room thermostat knob can indicate, for example, what temperature is being regulated. One pulse is one degree warmer, two short successive pulses are two degrees warmer. The temperature can be reduced if rotated in the other direction. The same applies to ovens, baking ovens etc.

Braille is even virtually possible using the haptic operating device. The torque profile against the rotational angle (rotation of the haptic knob) results in a Morse code or braille.

Furthermore, the dialing of a number can be described as follows: digits are equal to the number of haptic pulses.

Following a stroke or similarly severe illnesses/events, persons must relearn many functions. The opening of a door or door lock, the turning of a switch, for example of the washing machine, writing etc. must be learnt and trained again. An ideal tool for this is available with the adaptive haptic operating device. The latching pattern and the force or the torque can be adapted in an infinitely variable manner and a training program is therefore possible. This applies not only as trainers for the hand but also many more (joints, fingers, legs etc.).

The method according to the invention is particularly preferably carried out using an apparatus according to the invention, thus resulting in a particularly advantageous method of operation.

Not only data relevant to the situation can be displayed and adjusted on the display unit, but other data, for example the time, SMS, the telephone book, can also be displayed.

Other features which are considered as characteristic for the invention are set forth in the appended claims.

Although the invention is illustrated and described herein as embodied in a haptic operating device and method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 8A-8L show a control sequence with a haptic operating device according to the invention;

DETAILED DESCRIPTION OF THE INVENTION

Figure 1:
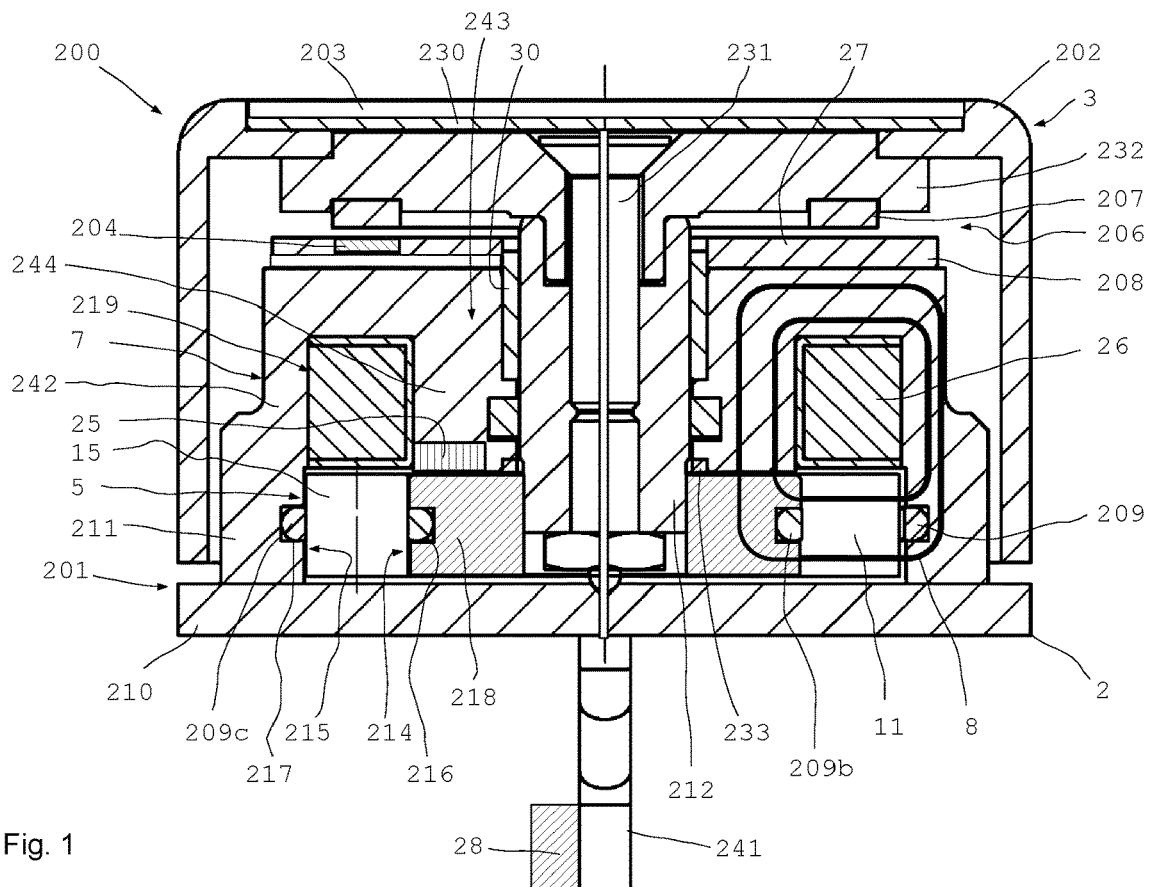
FIG. 1 shows a cross section through a specific embodiment of a haptic operating device according to the invention.

Exemplary embodiments of haptic operating devices 200 having magnetorheological transmission apparatuses 1 are explained below with reference to the accompanying figures, identical or similar parts being provided with the same reference symbols.

With regard to the specific application and the technological demands, any of a variety of transmission technologies may be implemented. Primarily the reaction speed of the device to control changes and the force or torque transmission that is required inform the choice of technology. As will become clear in the following, the implementation in the magnetorheological domain leads to very advantageous parameters: These include the very fast reaction speed of the system, the extreme bandwith in terms of force and torque, the completely continuous adjustability without any steps or gradations, the very low energy consumption of the system and the like. I will describe a magnetorheological transmission in the following, yet other transmissions are possible as well. These include electromagnetic systems, mechanical, fluid-mechanical, and also mixed systems.

Referring now to the figures of the drawing in detail and first, particularly, to FIG. 1 thereof, there is shown a schematic cross section of a first haptic operating device 200 according to the invention, the haptic operating device 200 containing a magnetorheological transmission apparatus 1, the precise function of which is explained further below with reference to FIG. 3.

FIG. 1 shows a cross section, the stationary basic body 201 being used as the component 2 here, on which the rotating unit 202 is rotatably held as the component 3. The basic body 201 has a holding housing 211 which is fastened to a separate base plate 210. For example, the holding housing 211 can be adhesively bonded to the base plate 210 after the parts arranged in the holding housing have been mounted. In comparison with the basic body 201, the rotating unit 202 is rotatably held here. The rotating unit 202 comprises a shaft 212 here, to which a holder 232 is screwed via a screw 231. The holder 232 is used to hold and accommodate the display unit 203 which is surrounded by the actual rotating unit 202. As a result, the rotating unit 202 can be externally gripped and rotated, whereas the display unit 203 remains substantially completely visible on the top side of the haptic operating device even if the user's hand rotates the rotary knob or the rotating unit 202.

The shaft 212 is rotatably mounted on the holding housing 211 via a bearing 30. The bearing 30 may be in the form of a sliding bearing, for example, but may also comprise any other rolling bearing.

An annular holding space 219, which is filled with an electrical coil 26 as a field generation device 7 here, is provided in the internal space 213 in the basic body 201, which is rotationally symmetrical here, and more precisely in the holding housing 211. Possible clearances can be filled, for example, with a potting compound or a filler which is simultaneously used to hold the electrical coil 26 in the annular holding space 219.

As depicted on the left side of FIG. 1, it is possible for an additional permanent magnet 25 or a plurality of additional permanent magnets 25 to be provided on the holding housing 211 in order to generate a permanent magnetic field independently of a current source. If necessary, the magnetization of the permanent magnet 25 can be changed using corresponding magnetic pulses from the electrical coil 26.

A channel 5 which is partially filled with rotating bodies 11 as rotatable transmission elements or as magnetic field concentrators, which are cylindrical here and, in particular, are arranged symmetrically over the circumference of the channel 5, is provided in the internal space 213 between the holding housing 211 and the shaft 212. The rotating bodies co-rotate during rotation of the two components 2, 3 with respect to one another since the rotating bodies 11 are usually in contact with the holding housing 211 and/or the shaft 212 and therefore roll thereon.

At least one contact element 209 in the form of a contact ring 209 (friction ring) can be provided for the purpose of assisting with the rolling and ensuring rolling contact. Such a contact ring may be in the form of an O-ring (round or angular or rectangular ring), in particular, and may consist of a rubber-like material, for example.

Such a contact ring 209 may be arranged, for example, in a circumferential groove 217 on the running surface 215 of the holding housing 211. It is also possible for a further contact ring 209b to be arranged in a groove 216 on the running surface 214 on an enlarged circumferential ring 218 of the shaft 212.

It is possible and preferred for a contact ring 209 to be arranged in the groove 217 and for a contact ring 209b to be arranged in the inner circumferential groove 216 on the running surface 214 of the circumferential ring 218.

Alternatively, it is also possible for the individual rotatable transmission elements or rotating bodies 11 as magnetic field concentrators to each be provided with a contact ring 209c, a contact ring 209c then extending around a rotating body 11. In the case of such a configuration as well, it is ensured that the rotating bodies 11 and their contact ring 209 each have contact with the shaft 212 or the holding housing 211, thus ensuring continuous rotation of the rotating bodies if the rotating unit 202 is rotated.

In the exemplary embodiment here, a defined axial distance between the holding housing 211 and an axial surface of the circumferential ring 218 is ensured via a stop ring 233. The internal space 213 is sealed via a seal 46, with the result that the magnetorheological medium cannot escape from the internal space 213.

A circumferential gap, at which a sensor 206 which is used as an angle sensor is arranged, is provided between the cover or the holder for 232 and the holding housing 211. The angle sensor 206 preferably consists of at least two parts 207 and 208, the sensor part 207 having magnets or other positional marks or the like at particular angle positions, for example, with the result that a rotational movement of the rotating unit 202 can be detected at the holding housing 211 via the sensor part 208 mounted on the electronics, for example. In this case, both an absolute angle position and a relative angle change can be sensed. The angle sensor 206 or a separate actuation sensor 204 can be used to sense an axial movement or an axial force on the rotating unit 202 or the operating device 200 as a whole. For example, a slight distance change between the holder 232 and the holding housing 211, which can be sensed by the actuation sensor 204, can be achieved by exerting an axial force. It is also possible for certain parts or the outer rotating ring of the rotating unit 202 to be axially displaceable counter to a spring force, with the result that axial actuation of the operating device 200 can be sensed. The electronics of the haptic operating device preferably operate with a control clock of 4 kHz or more.

The display unit which is rotatable together with the rotating unit 202 here can be supplied with the necessary data and the required electrical current via a cable feed 241 and a central channel. An energy store 28 can be internally or externally provided.

Figure 2:
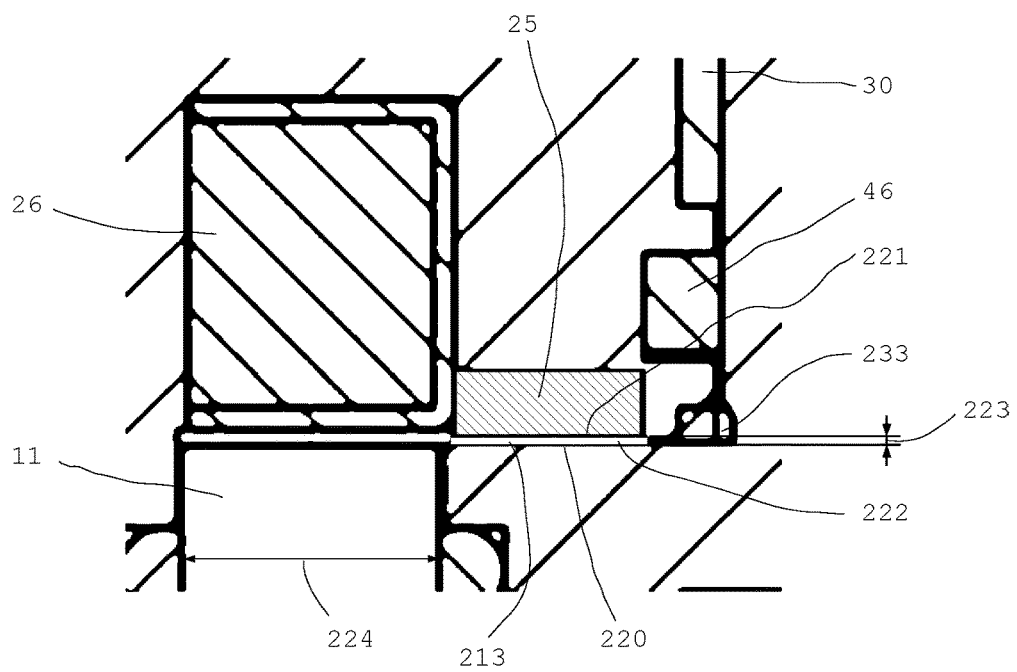
FIG. 2 shows an enlarged detail from FIG. 1.

FIG. 2 shows an enlarged detail from FIG. 1, in which case the rotating body 11—the rotating bodies 11 of all of the embodiments may be referred to as rotatable transfer elements or as magnetic field concentrators—and the electrical coil 26 and also a permanent magnet 25 are visible. The axial distance 223 between the end face 220 at the shaft 212 and the end face 221 at the holding housing 211 is clearly discernible here. This axial distance 223 is considerably shorter than the radial distance 224 between the circumferential ring 218 and the running surface 215 in the holding housing 211.

A short distance 223 is advantageous since the magnetic field 8 (compare FIG. 1) passes through the gap 222 in the axial direction. Relatively low magnetic losses are possible with a thin gap.

The functional principle for generating torques in the haptic operating device 200 is described below with reference to FIG. 3.

Figure 3:
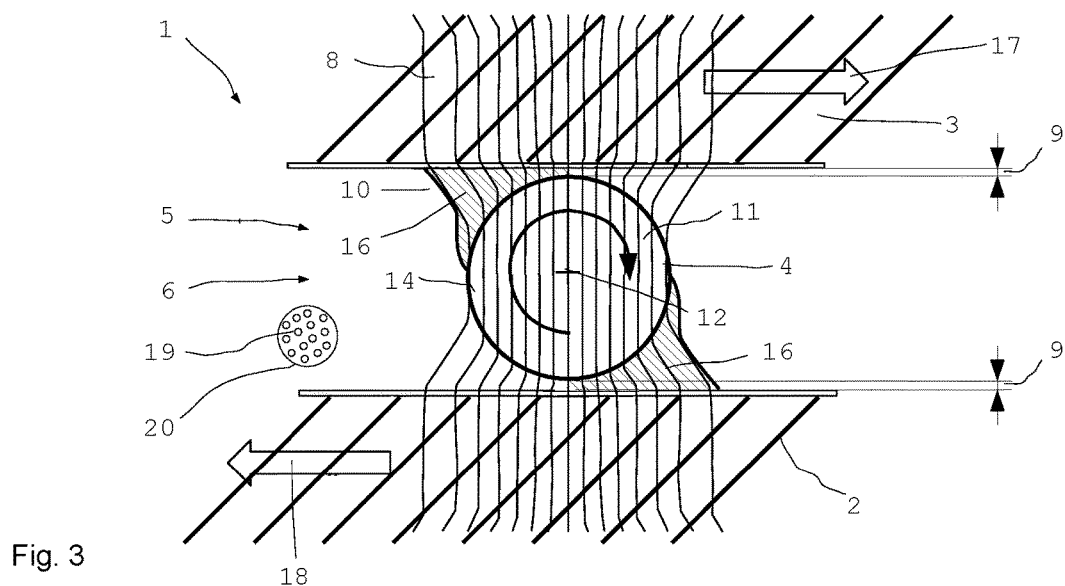
FIG. 3 shows a highly schematic view of the operating principle of a magneto-rheological transmission apparatus of the haptic operating device in cross section.

FIG. 3 shows a highly schematic cross-sectional view of a magnetorheological transmission apparatus 1 according to the invention for influencing the force transmission between two components 2 and 3. In this case, a rotating body 11 is provided as a separate part 4 between the two components 2 and 3 in FIG. 1. The rotating body 11 is in the form of a ball 14 here. However, it is likewise possible for rotating bodies 11 to be in the form of cylinders or ellipsoids, rollers or other rotatable rotating bodies. In the actual sense, rotating bodies which are not rotationally symmetrical, for example a gear wheel, or rotating bodies 11 having a particular surface structure can also be used as rotating bodies. The rotating bodies 11 are not used for mounting relative to one another, but rather for transmitting torque.

A channel 5 which is filled here with a medium 6 is provided between the components 2 and 3 of the magnetorheological transmission apparatus 1. The medium here is a magnetorheological fluid 20 which comprises, for example, as the carrier fluid, an oil-containing ferromagnetic particle 19. Glycol, fat, or viscous substances can also be used as the carrier medium without being restricted thereto. The carrier medium may also be gaseous or it is possible to dispense with the carrier medium (vacuum). In this case, only particles which can be influenced by the magnetic field are filled into the channel.

The ferromagnetic particles 19 are preferably carbonyl iron powder, the size distribution of the particles depending on the specific use. A particle size distribution of between one and ten micrometers is specifically preferred, but larger particles of 20, 30, 40 and 50 micrometers are also possible. Depending on the application, the particle size can also become considerably larger and can even advance into the millimeter range (particle spheres). The particles may also have a special coating/casing (titanium coating, ceramic casing, carbon casing etc.) so that they better withstand the high pressure loads which occur depending on the application. For this application, the MR particles can be produced not only from carbonyl iron powder (pure iron) but also from special iron (harder steel), for example.

The rotating body 11 is caused to rotate about its axis of rotation 12 by the relative movement 17 of the two components 2 and 3 and practically runs on the surface of the component 3. At the same time, the rotating body 11 runs on the surface of the other component 2, with the result that there is a relative velocity 18 there.

Strictly speaking, the rotating body 11 does not have any direct contact with the surface of the component 2 and/or 3 and therefore does not roll directly thereon. The free distance 9 between the rotating body 11 and one of the surfaces of the component 2 or 3 is 140 μm, for example. In one specific configuration with particle sizes of between 1 μm and 10 μm, the free distance is between 75 μm and 300 μm, in particular, and particularly preferably between 100 μm and 200 μm.

The free distance 9 is, in particular, at least 10 times the diameter of a typical mean particle diameter. The free distance 9 is preferably at least 10 times the size of a largest typical particle. As a result of the lack of direct contact, a very low base friction/force/torque is produced during relative movement of the components 2 and 3 with respect to one another.

If a magnetic field is applied to the magnetorheological transmission apparatus 1, the field lines are formed on the basis of the distance between the rotating bodies 11 and the components 2, 3. The rotating body consists of a ferromagnetic material and of ST 37 here, for example. The steel type ST 37 has a magnetic permeability pr of approximately 2000. The field lines pass through the rotating body and are concentrated in the rotating body. A high flux density prevails in the channel 5 on the radial entry and exit surface of the field lines on the rotating body. The inhomogeneous and strong field there results in local and strong crosslinking of the magnetically polarizable particles 19. The effect is greatly increased by the rotational movement of the rotating body 11 in the direction of the wedge forming in the magnetorheological fluid, and the possible braking or clutch torque is extremely increased far beyond the magnitude which can normally be produced in the magnetorheological fluid. The rotating body 11 and the component 2, 3 preferably at least partially consist of ferromagnetic material, which is why the magnetic flux density becomes higher, the shorter the distance between the rotating body 11 and the component 2, 3. As a result, a substantially wedge-shaped region 16 forms in the medium, in which the gradient of the magnetic field increases greatly toward the acute angle at the contact point/the region at the shortest distance.

Despite the distance between the rotating body 11 and the component 2, 3, the rotating body 11 can be caused to rotate by the relative velocity of the surfaces with respect to one another. The rotational movement is possible without and also with an acting magnetic field 8.

If the magnetorheological transmission apparatus 1 is exposed to a magnetic field 8 from a magnetic field generation device 7 (not illustrated here in FIG. 1), the individual particles 19 of the magnetorheological fluid 20 are concatenated along the lines of the magnetic field 8. It should be noted that the vectors depicted in FIG. 1 only roughly schematically illustrate that region of the field lines which is relevant to influencing the MRF 20. The field lines occur substantially in a manner perpendicular to the surfaces of the ferromagnetic components in the channel 5 and need not run in a rectilinear manner, in particular in the acute-angled region 10.

At the same time, on the circumference of the rotating body 11, some material of the magnetorheological fluid 20 is concomitantly caused to rotate, with the result that an acute-angled region 10 forms between the component 3 and the rotating body 11. On the other side, an identical acute-angled region 10 is produced between the rotating body 11 and the component 2. The acute-angled regions 10 may have a wedge shape 16 in the case of cylindrical rotating bodies 11, for example. The wedge shape 16 impedes the further rotation of the rotating body 11, with the result that the effect of the magnetic field on the magnetorheological fluid is intensified since the acting magnetic field inside the acute-angled region 10 results in greater cohesion of the medium 6 there. This intensifies the effect of the magnetorheological fluid in the accumulated cluster (the chain formation in the fluid and therefore the cohesion or viscosity), which makes it difficult to rotate or move the rotating body 11 further.

The wedge shape 16 makes it possible to transmit considerably greater forces or torques than would be possible with a comparable structure which uses only the shear movement without a wedge effect.

The forces which can be directly transmitted by the applied magnetic field represent only a small portion of the forces which can be transmitted by the apparatus. The magnetic field makes it possible to control the wedge formation and therefore the mechanical force intensification. The mechanical intensification of the magnetorheological effect can be such that it is possible to transmit a force, even after an applied magnetic field has been switched off, if the particles have been wedged.

It has been found that the wedge effect of the acute-angled regions 10 results in a considerably greater effect of a magnetic field 8 of a particular strength. In this case, the effect can be intensified by a multiple. In a specific case, the relative velocity of two components 2 and 3 relative to one another was influenced approximately 10 times as much as in the prior art in the case of MRF clutches. The possible intensification depends on different factors. It can possibly also be intensified by a greater surface roughness of the rotating bodies 11. It is also possible for outwardly projecting projections to be provided on the outer surface of the rotating bodies 11, which projections may result in even stronger wedge formation.

The wedge effect is distributed in a two-dimensional manner between the rotating body 11 and the components 2 or 3.

Figure 4:
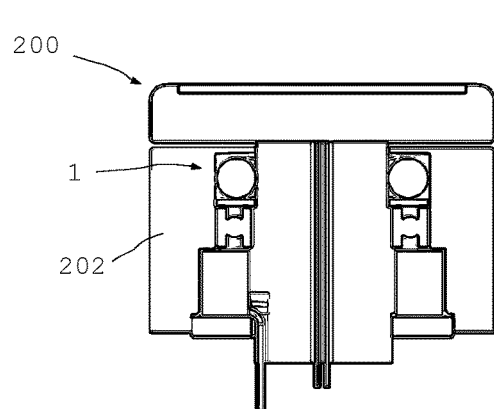
FIG. 4 shows another embodiment of a haptic operating device according to the invention.
Figure 5:
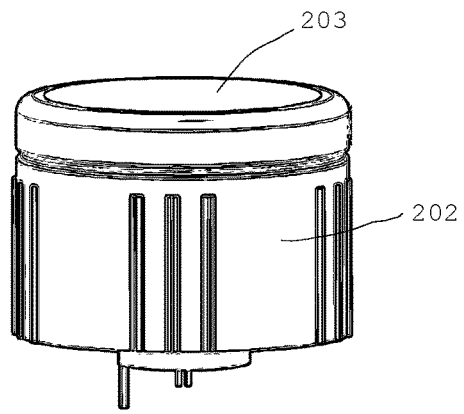
FIG. 5 shows a slightly perspective illustration of the haptic operating device according to FIG. 4.

FIG. 4 shows a schematic illustration of another embodiment of a haptic operating device according to the invention in which the display unit 203 is stationary and in which the rotating unit 202 arranged axially beside the display unit can be rotated without the display unit 203 co-rotating. A magnetorheological transmission apparatus 1 is also provided in the operating device 200 according to FIGS. 4 and 5 in order to generate the required magnetic forces and the accordingly acting braking forces or braking torques.

Figure 6:
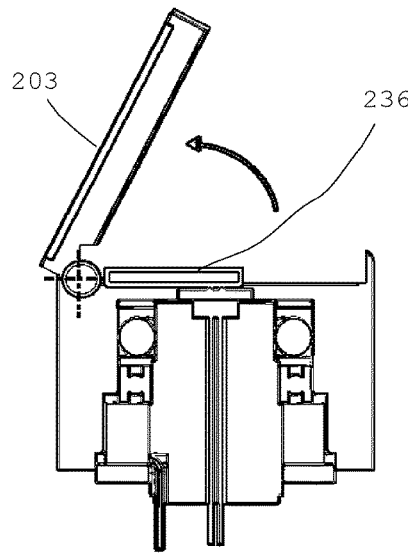
FIG. 6 shows another embodiment of a haptic operating device according to the invention.

FIG. 6 shows a variant of the exemplary embodiment according to FIG. 4, in which case the cover with the display unit 203 is hinged, with the result that, after opening, a fingerprint sensor 236 or the like (touchpad etc.) is available in order to authenticate a user, for example.

Figure 7:
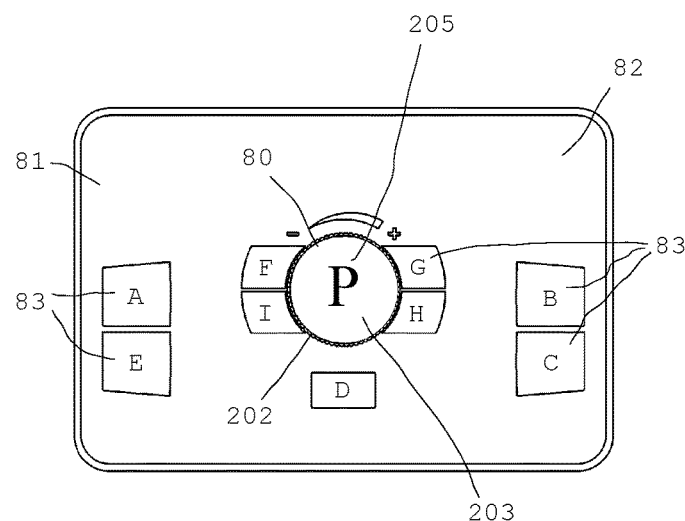
FIG. 7 shows another embodiment of a haptic operating device according to the invention.

FIG. 7 shows an operating device 1 according to the invention having an operating knob 80 as a haptic operating device 200 and having a display 81, from which the haptic operating device 200 projects upward. This means both that the display 81 is suitable for representing information here and that the display unit 203 on the top side of the operating device 200 is used to reproduce information and to select menu items. Buttons 83 can be actually or virtually provided on the touchscreen 82 and can be actuated by pressing in order to initiate particular actions. In any case, it is possible to select menu items on the display unit 203 by rotating the rotating unit 202 of the operating device 200.

The operating device 200 according to FIG. 7 has an operating knob or a rotary knob 80 having a magnetorheological transmission apparatus 1. The housing as a component can be permanently fitted to a device, for example. The shaft as a component is connected to the rotating part. Both components 2 and 3 are rotatably mounted with respect to one another via bearings. A thin gap as a free distance 9 is situated between the rotating body 11 and the housing and also between the rotating body 11 and the shaft. The space surrounding the rotating bodies 11 and possibly virtually the entire internal space can be filled with a magnetorheological fluid as the medium 6. A sealing ring 46 acts as a seal with respect to the bearing which is thus protected from the particles in the magnetorheological fluid.

Activation of the coil 26 generates a magnetic field 8 which, as shown by the field lines depicted by way of example, passes through the rotating bodies 11 and here otherwise substantially runs inside the housing and the shaft. With an activated magnetic field of the coil 26, a corresponding resistance is produced in the medium 6 or the MR fluid, with the result that a corresponding resistance can be felt when rotating the rotating part 85. Temporally pulsed or pulsating operation, as a result of which a pulsating resistance and therefore latching will become noticeable, is also possible, for example.

The respectively current angle position can be sensed via a rotary encoder. As a result, arbitrary haptic signals can be output on the basis of the control, depending on the position, rotational angle, angular velocity etc. The rotary encoder can also be supplemented with a torque sensor.

Two-dimensional haptic knobs or rotary knobs 80 can also be produced with an additional MRF shear mode.

An MRF haptic knob can have a very small construction for actuating devices in SLR cameras and other cameras and in games consoles and other handheld computers. Such MRF coupling devices having a small construction are highly suitable for cameras and other outdoor applications on account of the small space requirement and the low power consumption in the range of milliwatts or below. The latching pattern can be set on the basis of the situation.

Three-dimensional movement elements with variable haptics and robust and precise mounting are fundamentally difficult to produce and are therefore not inexpensive. In contrast, the combination of an arrangement of the rotating bodies which is capable of pendulum movements with a magnetorheological fluid, for example, can be produced in a very cost-effective manner.

A four-dimensional rotary knob which can be displaced and can also be additionally rotated in three directions, for example, can also be provided.

The combination of a 3-D knob with longitudinal adjustment of an MRF wedge therefore results in a 4-D actuating element. A field generation unit can be used to influence or vary all four directions of movement.

It is also possible to use such haptic knobs on touch-sensitive displays such as touch displays in mobile telephones, PDAs, smartphones, portable and stationary computers and on screens, games consoles, tablet PCs, laptops etc. For this purpose, at least one haptic element in the form of a rotary knob, for example, is provided there.

Such a haptic element 200 can also be foldable/pivotable or displaceable and can be displaced, for example, from a position of rest on the edge into a position above the display. As soon as the haptic element is above the display, the display on the display can change, that is to say a menu appears below or around the knob.

Instead of a kinematic and, for example, parallelogram-like pivoting mechanism, it is also possible to use an elastic/deformable element which, as a flexible and semi-rigid arm, for example, can consist of coiled metal tubing in the form of a swan's neck. One advantage is that the user does not always have to grip the screen, which reduces soiling. In addition, the adjustment and the zooming, for example, take place more quickly: gripping the screen with one finger and moving the rotating controller with another finger can initiate a zooming process, for example. The same applies to the volume, writing with uppercase and lowercase letters or selecting special buttons or a second level during typing.

The user can thus also press with one finger on a separate menu bar in order to search for the type of desired actuation. He then performs the desired action using the rotating controller. The latching pattern of the rotating controller then adapts automatically, thus, for example, "on"—"off" or volume control with a latching pattern possibly having a dynamic stop. If the screen is rotated during the actuation (touch display) (for example, as in the case of mobile telephones or handheld computers—90° from portrait format to landscape format), the latching pattern adapts automatically, i.e. it co-rotates. For example, if the setting range were from 6 o'clock to 12 o'clock when it is held upright, this would change from 12 o'clock to 6 o'clock upon rotation by 90° in the clockwise direction without adaptation. This also applies if the display is installed in the knob itself. Such a haptic element can be haptic in all or individual directions (only rotate, rotate and press; joystick etc.). The haptics adjust themselves depending on the selected action.

One advantage can also result upon the selection of a list such as a telephone book list, for example, since such entries are often too small for "targeting" for large fingers.

Advantages also result in the dark or for people with spectacles who are not currently wearing them. Feedback is received via the haptic rotating controller and the user knows what he is doing when it is currently dark, for example.

The functionality and the method of operation of an operating device 200 according to the invention are explained below with reference to FIGS. 8A to 8L using the example of the use in a motor vehicle.

In this case, FIG. 8A shows a plan view of the haptic operating device 200 according to the invention of a motor vehicle. The haptic operating device 200 may be used, in particular, to select an operating state of the motor vehicle. If a user sits in the motor vehicle and on the driver's seat, for example, the haptic operating device 200 can directly detect the presence of the driver and/or of the key or of another suitable identification object using a sensor (not illustrated) and can be automatically changed from the switched-off state of rest to a more active state. In this state, the display unit 203 of the haptic operating device 200 displays the operating state of the motor vehicle, for example.

FIG. 8A illustrates the operating state "off". The display unit 203 centrally displays a graphical symbol 205 with the operating state on the rotating unit 202. A menu ring 235, on which the individual selectable menu items 225 are depicted, is graphically illustrated further on the outside. There are three menu items in FIG. 8a, in which case the indicator 234 is illustrated beside the selected operating state or beside the currently active operating state.

Rotating the rotating unit 202 in the direction of rotation 227 (here to the right or in the clockwise direction) then makes it possible to select the menu item for setting the radio or the audio system. This state is illustrated in FIG. 8B where the clef is depicted as the graphical symbol 205 in the center of the display unit 203. The indicator 234 indicates that the corresponding menu item 225 is active.

Rotating the rotating unit 202 further finally makes it possible to activate the starting function of the motor vehicle, as shown in FIG. 8C. The engine can be started by pressing the touch-sensitive surface of the display unit 203.

After the engine has been started by actuating the touch-sensitive button of the display unit 203 and/or by axially pressing the rotating unit 202 or the entire operating device 200, the engine is started, thus resulting in the state for an automatic vehicle, which is illustrated in FIG. 8D. In this case, the parking function is activated, with the result that the vehicle is not unintentionally caused to move. Irrespective of how the automobile was parked, the parking function is activated in any case after restarting, with the result that reliable prevention of unintentional driving is ensured.

This is very advantageous since no mechanical resetting is required for this. Although the haptic operating device 200 detects the angle position of the rotating unit 202, this is only necessary and useful during operation. After the vehicle has been restarted, all settings are reset to the basic settings, with the result that the state "P" always results after the engine has been restarted irrespective of the angle position of the rotating unit and the state in which the vehicle is stopped and the engine is switched off.

Actuating the rotating unit 202 and rotating it in the clockwise direction results in the reverse gear being reached as the next latching point, as illustrated in FIG. 8E. Rotation into the position "N" can be blocked in this case (very high braking torque) if the foot brake or parking brake is not actuated at the same time, for example. Further rotation changes the rotating unit to the menu item "N" (idling), as shown in FIG. 8F.

The next latching point corresponds to the menu item "D", as shown in FIG. 8G. Actuating the rotating unit 202 in the axial direction or pressing the touch-sensitive display activates the operating mode "D" and the driver can drive away.

If, in contrast, the menu item "S" is actuated, a submenu is activated and the selection possibilities from eight different gears here are provided, as illustrated in FIG. 8H. Appropriate rotation of the rotating unit 202 can activate one of the eight gears by means of the corresponding menu item Si to S8. In this case, each gear may be assigned an arbitrary latching pattern/torque profile, for example, with the result that the operator recognizes the selected position without looking.

A rotational movement in the opposite direction, that is to say in the anticlockwise direction, leads back to the other menu items.

In all cases, the number of latching points for the rotating unit 202 is adapted to the number of available menu items. This means that eight different latching points are provided in FIG. 8H, whereas six different menu items can be illustrated and selected in FIG. 8K, for which six latching points are accordingly provided. Right-hand and left-hand end stops are dynamically generated here, with the result that the rotating unit cannot be rotated further as desired in the switched-on state.

If the rotating unit 202 is rotated back to the starting point, as illustrated in FIG. 8L, the symbol for stopping the engine is dynamically displayed. The engine is stopped by pressing the symbol or by actuating the rotating unit 202 or the operating device 200 and the state from FIG. 8A is reached again.

The starting or stopping knob need not necessarily be on the display unit, but rather may also be an independent knob, for example in the vehicle console.

Overall, a haptic rotary knob is provided, the haptic latching pattern of which is oriented on the basis of the available menu items in a menu. The available latching points are generated dynamically or adaptively.

Figure 9A:
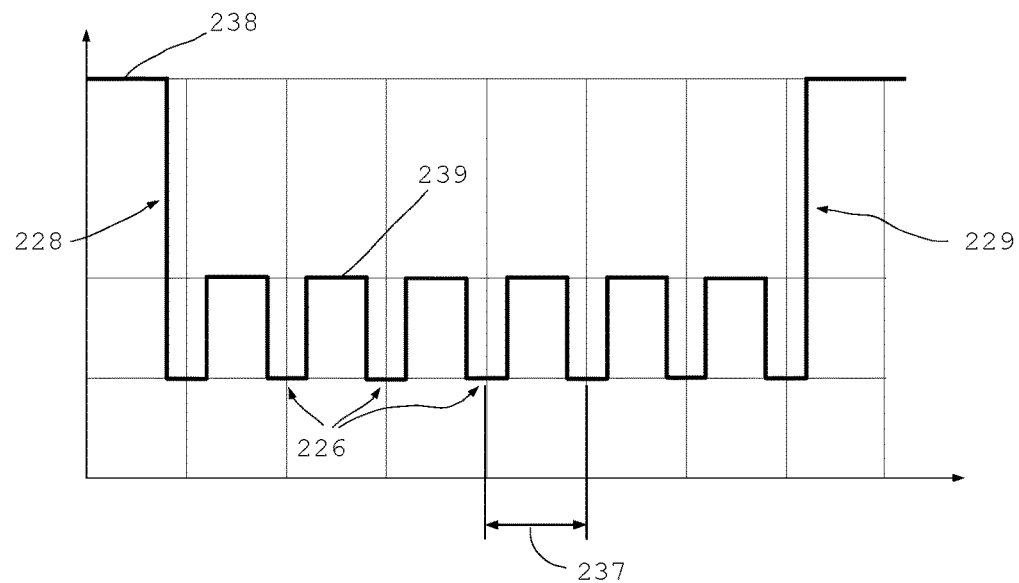
FIGS. 9A-9C show possible torque profiles against the rotational angle of a haptic operating device according to the invention.
Figure 9B:
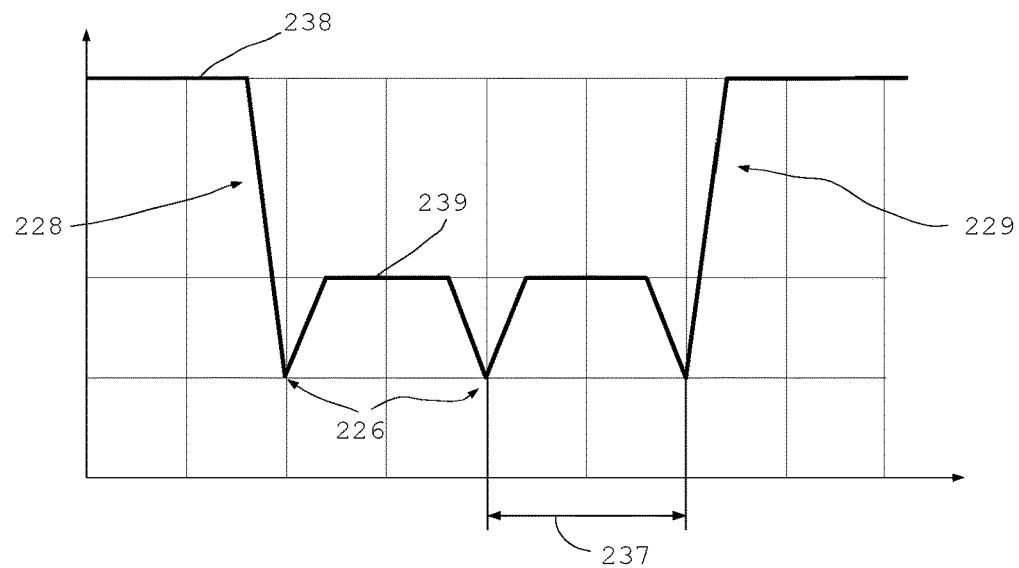
Figure 9C:
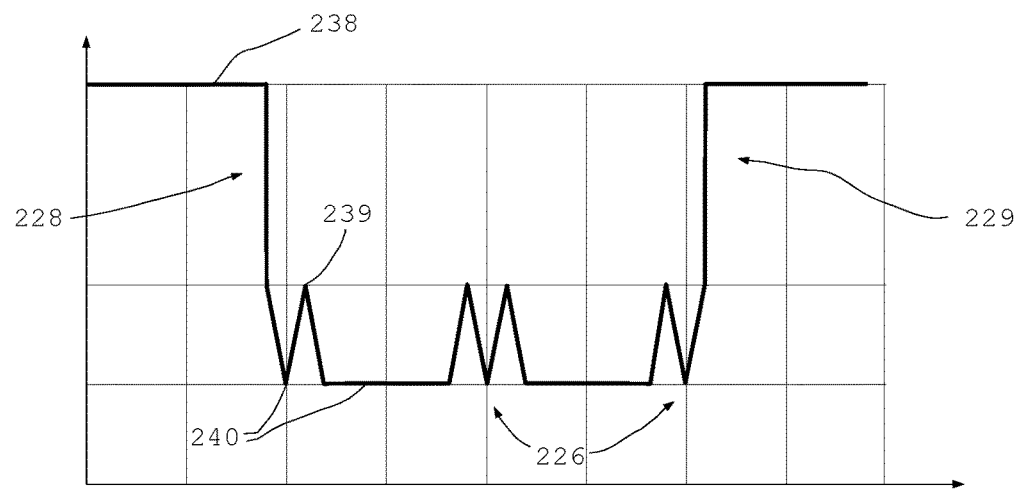

FIGS. 9A, 9B and 9C illustrate possible embodiment variants for the dynamically generated magnetic field or the dynamically generated braking torque on the basis of the rotational angle.

In this case, FIG. 9A shows a variant in which a left-hand end stop 228 and a right-hand end stop 229 are generated. During further rotation, a high magnetic field or stop torque 238 is generated there, as a result of which the rotating unit 202 opposes a high resistance to a rotational movement.

A first latching point 226 corresponding to a first menu item 225 is provided directly beside the left-hand end stop 228. If the next menu item is intended to be selected, the rotating unit 202 must be rotated in the clockwise direction. For this purpose, the dynamically generated higher magnetic field or latching torque 239 or its frictional torque must be overcome before the next latching point 226 is reached. In FIG. 9A, a constant magnetic field is respectively generated at the latching points 226 and in the regions in between for a certain angular range, which magnetic field is considerably lower at the latching points than in the regions in between and is again considerably lower than at the stops 228, 229.

An angular distance 237 between individual latching points can be dynamically changed and is adapted to the number of available latching points or menu items.

FIG. 9B shows a variant in which the magnetic field does not suddenly increase toward the end stops 228, 229 but rather has a steep profile. Furthermore, ramp-like gradients of the magnetic field are respectively provided at the latching points 226 toward both rotation sides, as a result of which the rotational resistance increases in the corresponding directions of rotation. Only three latching points 226 are provided here with the same operating device 200, the angular distance 237 of which latching points is greater than in the example according to FIG. 9A.

FIG. 9C shows a variant in which there is a lower rotational resistance between individual latching points 226 and an increased magnetic field 239 is respectively generated only directly adjacent to the latching points 226 in order to enable engagement at the individual latching points 226 and, at the same time, to provide only a low rotational resistance between individual latching points.

In principle, it is also possible to mix the methods of operation and the magnetic field profiles shown in FIGS. 9A, 9B and 9C. For example, the magnetic field profile can accordingly be set differently for different submenus.

If the rotating unit is not rotated, that is to say the angle is constant, the current is preferably continuously reduced over time. The current can also be varied on the basis of the velocity (rotational angle velocity of the rotating unit).

Figure 10:
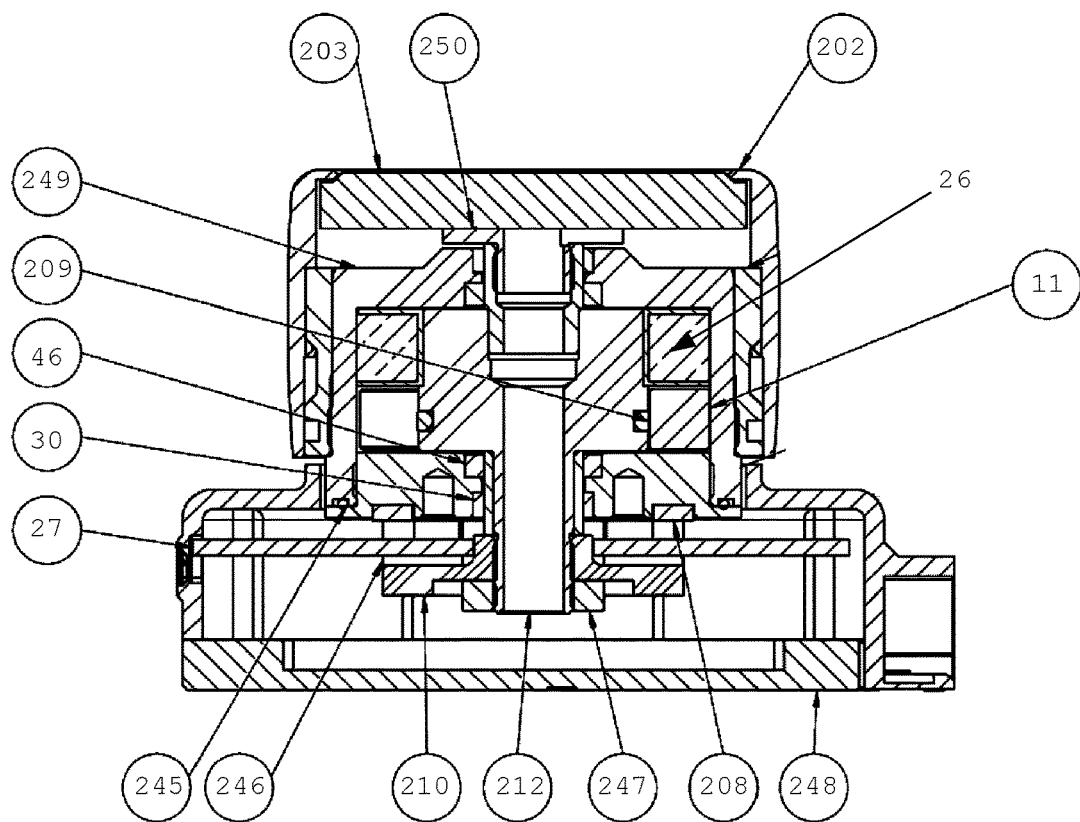
FIG. 10 is a section taken through another embodiment of a haptic operating device according to the invention.

FIG. 10 shows another embodiment variant of the haptic operating device 200 having a stationary display unit 203. The watch plate 250 is arranged beneath the display unit 203. The outer part 249 having the rotating unit 202, which is in the form of an aluminum knob in this case, is rotatably held on the shaft 212. The rotating bodies 11 are again in a channel 5 and act as magnetic field concentrators. The coil 26 is used to generate a magnetic field. The O-ring 245 provides sealing. A spacer sleeve 246 is used to set the distance. The lock nut 247 is used to secure the shaft 212. The lock nut 247 is covered by the housing base toward the bottom.

Figure 11:
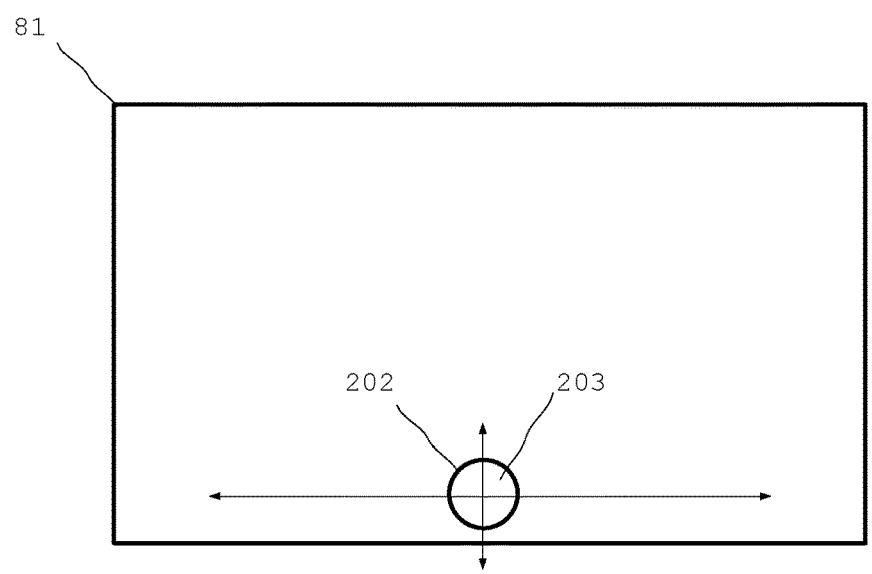
FIG. 11 shows an embodiment of a haptic operating device according to the invention which can be moved and/or tilted.

FIG. 11 shows an exemplary embodiment in which the operating device 200 can be moved in at least one dimension. It may thus be formed on an infotainment system of a motor vehicle, for example. The operating knob can be horizontally (and/or) vertically movable, as indicated by the arrows in FIG. 11. It is also possible for the operating knob to be tiltable (and possibly not movable). Tilting can also be carried out in two or more directions. A suitable menu item can be selected by means of moving (tilting). If the operating knob is moved laterally, for example, the next menu item in each case can be selected and can be displayed on the display 81 and/or 203. In this configuration, it is possible to dispense with the display 203. Even faster selection is enabled as a result. Like the rotation of the haptic knob, the movement can also be haptically highlighted (for example a short stop at the menu items). When using a touchscreen or a similarly touch-sensitive display and an operating element which moves across the latter, the touchscreen itself can be used to detect the position. The operating knob transmits the position to the display, for example during movement, as is carried out by a finger, for example in the case of a "slider" (unlocking of a mobile phone). However, the movement position can also be detected using position elements according to the prior art (length measuring systems, image recognition etc.).

This also applies to an (axial) pressing function (for example for confirming a selected choice). The touchscreen can be used in this case too, the operating knob which moves across it virtually being the "human finger".

This movability is also advantageous when a change is made between self-driving and autonomous driving in an automobile, for example. During self-driving, the haptic operating element is used as a gear selection lever; this function is no longer required during autonomous driving and the operating element can be used for other functions. The operating element can then remain at the same position and can undertake the new functions. However, this is possibly confusing for the user and it is better if the knob has a different function only after having been moved to a different position. The function of the operating element can thus also be assigned and used again without looking. The practice of moving the operating element is more cost-effective and more space-saving in this case than implementing two haptic knobs (one of which is mostly always unused).

Overall, the invention provides an advantageous haptic operating device 200 and an accordingly advantageous method for controlling a motor vehicle or else domestic appliances, for example, in which case a display unit on which the selectable menu items are displayed is centrally provided on the haptic operating knob. The number and type of latching points are dynamically adapted to the number of available menu items.

In all cases, the effective torque can be set on the basis of the speed using pulse width modulation (PWM), for example. Large axial and radial forces can be generated using an oblique expanding mandrel. The particles may have a round, rod-shaped or any other form.

The rheological fluid may consist of a wide variety of constituents which individually or in combination may be: Fe, carbon steel, NdFeB (neodymium), AlNiCo, samarium, cobalt, silicon, carbon fiber, stainless steel, polymers, soda-lime glass, ceramic and non-magnetic metals and the like. Dimorphic magnetorheological fluids containing nanotubes or/and nano wires are also possible.

The carrier fluid may consist, in particular, of the following constituents or a combination thereof: oils and preferably synthetic or non-synthetic oils, hydraulic oil, glycol, water, fats and the like.

The device according to the invention and as illustrated, for instance, in FIG. 1 was constructed several times. It exhibited a measured base torque of approx. 0.015 Nm and a maximum torque of greater than 5 Nm. That is, a factor of well over 300 has been shown to be available with the invention.

The sensor system, for example the sensor 206, has a high detection resolution. This makes it possible to detect certain movement patterns with great accuracy. If, by way of example, the user moves the rotating component according to a given pattern (e.g., quick tremble back-and-forth, or repeated left/right turn), the control unit triggers a new operation, such as selecting a given submenu or a superordinate-level menu. By way of example, when the actuator is currently used to scan available radio stations, the user may select a currently displayed station by a quick "wiggle" of the actuator (e.g., three times left, three times right). Due to the high resolution of the sensors, only very slight movements for the detection pattern are sufficient for the control system to "know" with great certainty the user's input.

The following is a summary list of reference numerals and the corresponding structure used in the above description of the invention:

1 Transmission apparatus, equipment
2, 3 Component
4 Separate part
5 Channel
6 Medium
7 Magnetic field generation device
8 Field
9 Free distance
10 Acute-angled region
11 Rotating body
12 Axis of rotation
13 Rotating body
14 Ball
15 Cylinder
16 Wedge shape
17 Direction of the relative movement
18 Direction of the relative movement
19 Magnetic particle
20 Fluid
25 Permanent magnet
26 Coil
27 Control device
28 Energy store
30 Bearing
46 Sealing ring
80 Operating knob
81 Display
82 Touchscreen
83 Button
200 Operating device
201 Basic body
202 Rotating unit
203 Display unit
204 Actuation sensor
205 Graphical symbol
206 Angle sensor
207 Sensor part
208 Sensor part, electronics
209 Contact ring, friction ring
210 Base plate
211 Holding housing
212 Shaft
213 Internal space
214 Running surface of 212
215 Running surface of 211
216 Groove
217 Groove
218 Circumferential ring with 214 and 216
219 Holding space for 26
220 End face of 218
221 End face of 211
222 Gap
223 Axial distance
224 Radial distance
225 Menu item
226 Latching point
227 Direction of rotation
228 End stop
229 End stop
230 Cover
231 Screw
232 Holder
233 Stop ring
234 Indicator
235 Menu ring
236 Fingerprint sensor
237 Angular distance
238 Stop torque
239 Latching torque
240 Base torque
241 Cable
242 Outer limb
243 Radially inner region
244 Inner limb
245 O-ring
246 Distancing sleeve 247 Counter nut
248 Housing floor, base
249 Outer part
250 Watch plate

The invention claimed is:

1. A method of adjusting a smart device, the method comprising:
   providing a haptic feedback device with a rotary element for manual activation, the haptic feedback device containing an energy storage device and being configured for inductive charging;
   establishing wireless communication between the haptic feedback device and the smart device;
   encoding a rotation of the rotary element upon a manual activation thereof with a rotary encoder;
   controlling an input of the smart device in accordance with the manual activation of the rotary element and setting a property of the rotary element in accordance with a currently selected menu on the smart device;
   wherein the property of the rotary element is a resistance against a rotation thereof and wherein the resistance is dynamically variable to thereby provide haptic feedback to a user controlling the smart device;
   wherein the dynamically variable resistance is provided by an electronically controlled resistance against the rotation of the rotary element; and
   wherein a response time of the rotary element to switch from an arbitrary initial torque opposing the rotation of the rotary element to an end torque opposing the rotation is less than 20 milliseconds.

2. The method according to claim 1, which comprises supplying the haptic feedback device with energy by inductive coupling and by additionally acquiring energy required for an operation of the haptic feedback device by an energy harvesting process.

3. The method according to claim 1, wherein the smart device has a display screen and the method further comprises:
   placing the haptic feedback device directly on the display screen of the smart device and operating the rotary element with the haptic feedback device disposed on the display screen.

4. A method of adjusting a smart device, the method comprising:
   providing a haptic feedback device with a rotary element for manual activation, the haptic feedback device containing an energy storage device and being configured for inductive charging;
   establishing wireless communication between the haptic feedback device and the smart device;
   encoding a rotation of the rotary element upon a manual activation thereof with a rotary encoder;
   controlling an input of the smart device in accordance with the manual activation of the rotary element and setting a property of the rotary element in accordance with a currently selected menu on the smart device;
   providing the haptic feedback device with a display unit having a display disposed inside the rotary element;
   sensing a rotation being an angle change of the rotary element; and
   rotating display contents on the display of the display unit in an opposite direction of the angle change to thereby retain the display contents stationary relative to the smart device.

5. The method according to claim 4, wherein the property of the rotary element is a resistance against a rotation thereof and wherein the resistance is dynamically variable to thereby provide haptic feedback to a user controlling the smart device.

6. The method according to claim 5, wherein the dynamically variable resistance is provided by an electronically controlled resistance against a rotation of the rotary element.

7. The method according to claim 6, wherein the electronically controlled resistance is provided by driving a magnet device or an electrical device that converts to a mechanical feedback or mechanical resistance of the rotary element.

8. The method according to claim 6, wherein the electronically controlled resistance is provided by a magnetorheological transmission apparatus functionally associated with the rotary element.

* * * * *